(12) United States Patent
Arai et al.

(10) Patent No.: US 11,744,546 B2
(45) Date of Patent: Sep. 5, 2023

(54) CONTROL DEVICE, MEDICAL IMAGING SYSTEM, CONTROL METHOD, AND CONTROL PROGRAM

(71) Applicant: FUJIFILM CORPORATION, Tokyo (JP)

(72) Inventors: Takahisa Arai, Kanagawa (JP); Hiroki Nakayama, Kanagawa (JP); Yoshie Fujimoto, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 771 days.

(21) Appl. No.: 16/804,031

(22) Filed: Feb. 28, 2020

(65) Prior Publication Data
US 2020/0305835 A1 Oct. 1, 2020

(30) Foreign Application Priority Data
Mar. 29, 2019 (JP) .................................. 2019-067291

(51) Int. Cl.
*A61B 8/00* (2006.01)
*A61B 8/08* (2006.01)
*G06T 7/00* (2017.01)

(52) U.S. Cl.
CPC ............ *A61B 8/403* (2013.01); *A61B 8/0825* (2013.01); *A61B 8/461* (2013.01); *G06T 7/0012* (2013.01);
(Continued)

(58) Field of Classification Search
CPC ....... A61B 8/403; A61B 8/0825; A61B 8/461; G06T 7/0012; G06T 2207/10028;
(Continued)

(56) References Cited

U.S. PATENT DOCUMENTS

| 2012/0014578 A1* | 1/2012 | Karssemeijer | ........ G06T 7/0012 382/131 |
| 2014/0093033 A1* | 4/2014 | Takata | ................. A61B 6/0414 378/208 |

(Continued)

FOREIGN PATENT DOCUMENTS

| JP | 2010-253245 A | 11/2010 |
| JP | 2015-154916 A | 8/2015 |

*Primary Examiner* — Keith M Raymond
*Assistant Examiner* — Sean A Frith
(74) *Attorney, Agent, or Firm* — SOLARIS Intellectual Property Group, PLLC

(57) ABSTRACT

A control device including: a breast thickness acquisition unit that acquires a thickness of a breast in a pressed state by a pressing member; a depth information acquisition unit that, in a case where an ultrasound image of the breast in the pressed state is captured, acquires depth information indicating a depth to which imaging by an ultrasonography apparatus which captures the ultrasound image is possible; a deriving unit that derives imaging information indicating whether or not capture of an ultrasound image having predetermined accuracy or higher is possible by the ultrasonography apparatus on the basis of the thickness of the breast acquired by the breast thickness acquisition unit and the depth information acquired by the depth information acquisition unit; and an output unit that outputs the imaging information derived by the deriving unit.

20 Claims, 19 Drawing Sheets

(52) U.S. Cl.
CPC ........... *G06T 2207/10028* (2013.01); *G06T 2207/10136* (2013.01); *G06T 2207/30068* (2013.01); *G06T 2207/30096* (2013.01)

(58) Field of Classification Search
CPC . G06T 2207/10136; G06T 2207/30068; G06T 2207/30096
See application file for complete search history.

(56) References Cited

U.S. PATENT DOCUMENTS

| | | | |
|---|---|---|---|
| 2015/0105649 A1* | 4/2015 | Suzuki | A61B 5/741 600/407 |
| 2015/0182191 A1* | 7/2015 | Caluser | A61B 5/4312 600/407 |
| 2016/0030000 A1* | 2/2016 | Sandhu | A61B 8/5207 600/448 |
| 2017/0251991 A1* | 9/2017 | Wang | A61B 8/0825 |
| 2018/0184999 A1* | 7/2018 | Davis | A61B 6/4417 |

\* cited by examiner

| ULTRASONOGRAPHY APPARATUS | APPARATUS A | APPARATUS B | APPARATUS C | APPARATUS D | ... | 53 |
|---|---|---|---|---|---|---|
| LIMIT DEPTH | 40 mm | 10 mm | 80 mm | 60 mm | ... | |

FIG. 10
| THICKNESS OF BREAST | ULTRASONOGRAPHY APPARATUS B | |
|---|---|---|
| 30 mm | IMAGING POSSIBLE RANGE | 20 TO 30 mm |
| | IMAGING IMPOSSIBLE RANGE | 0 TO 20 mm |
FIG. 11A
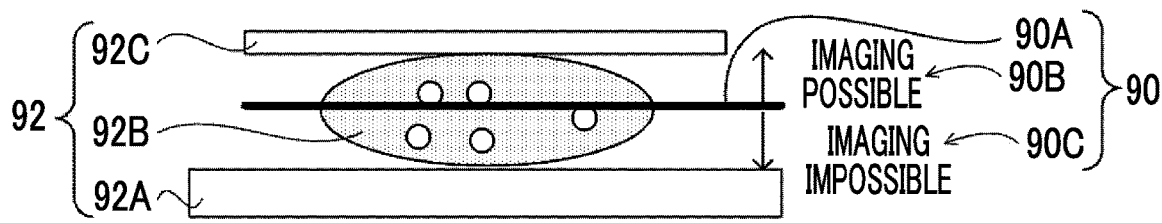
FIG. 11B
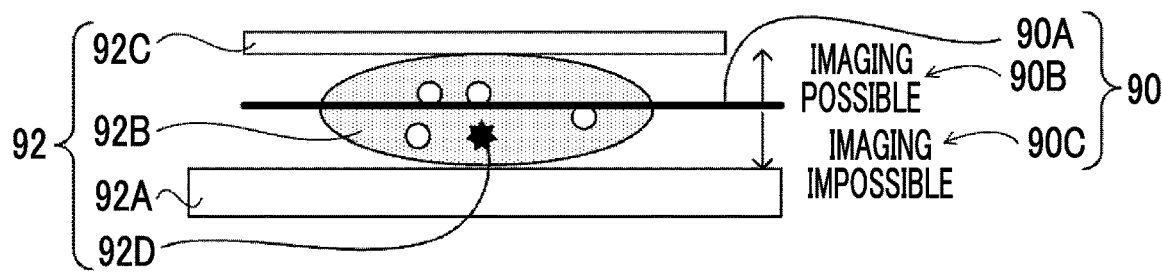

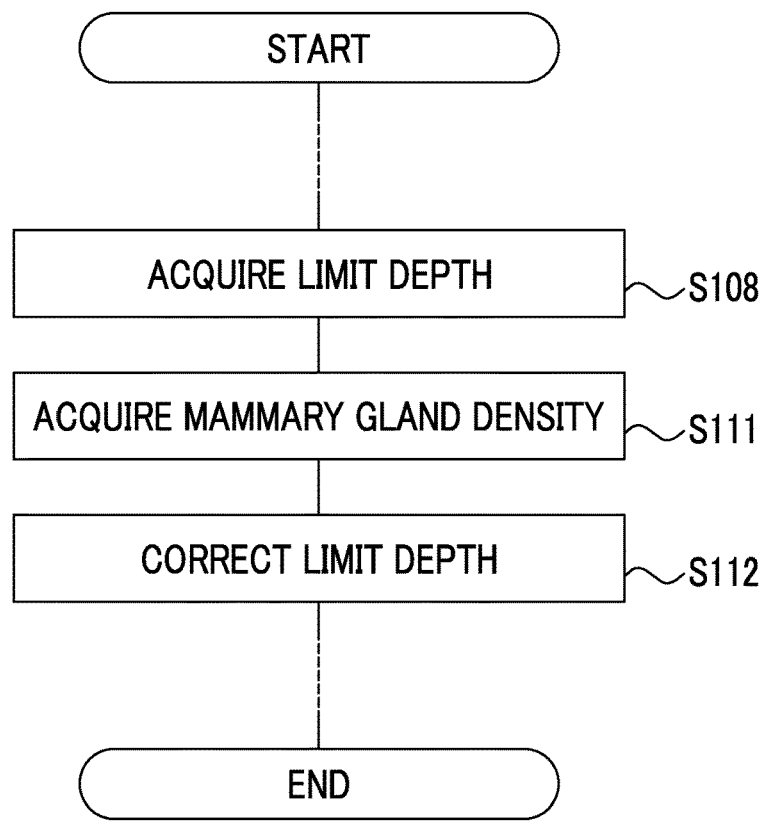
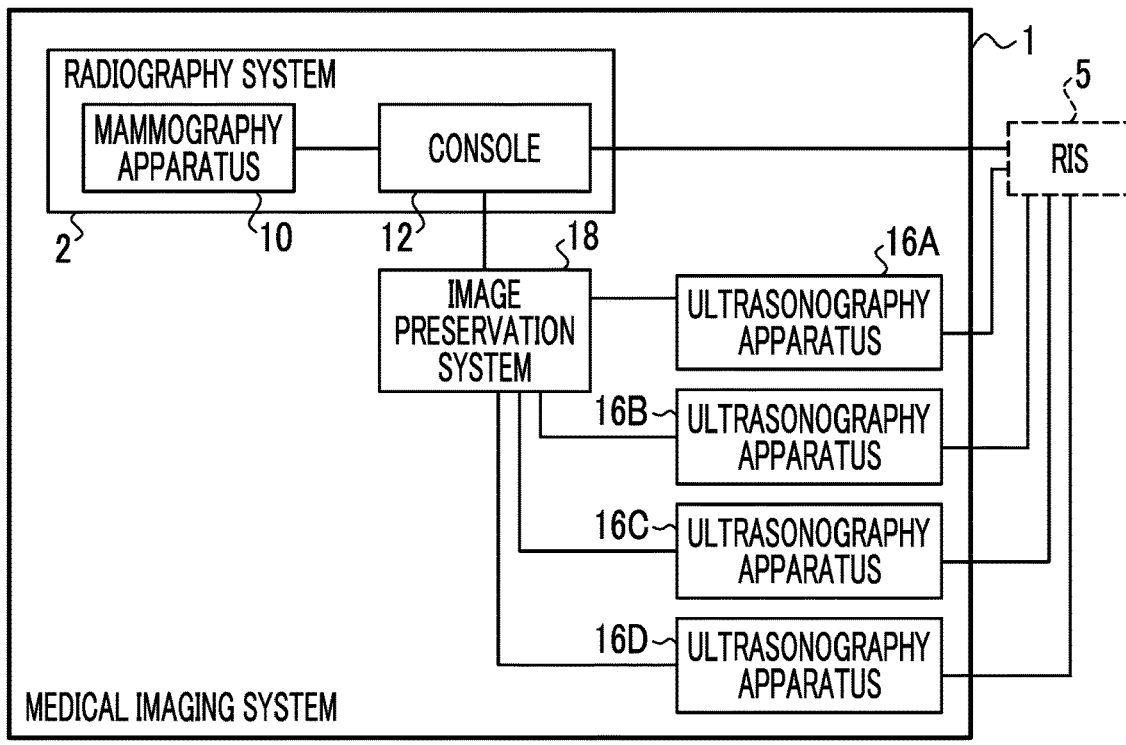

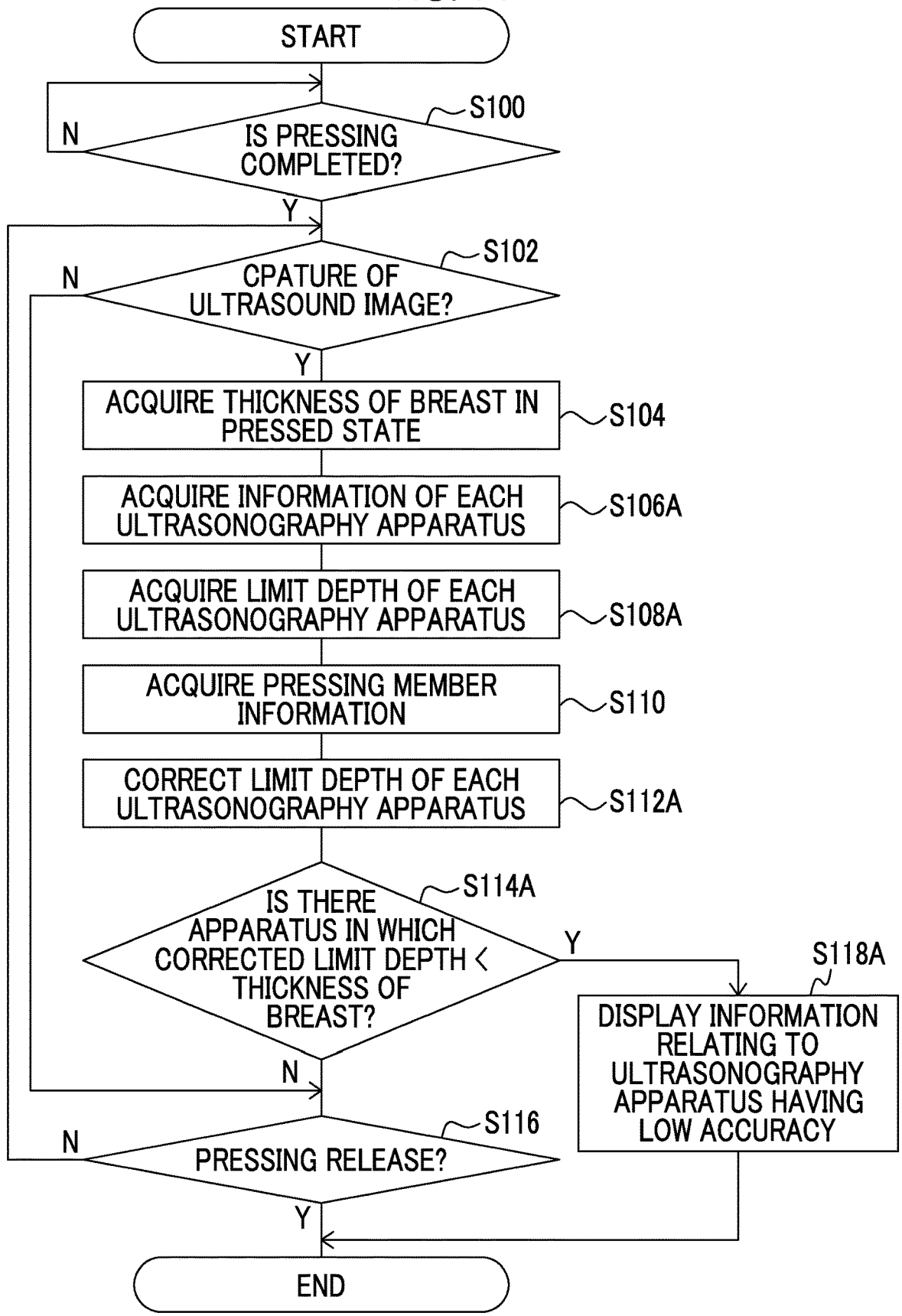

CONTROL DEVICE, MEDICAL IMAGING SYSTEM, CONTROL METHOD, AND CONTROL PROGRAM

CROSS-REFERENCE TO RELATED APPLICATION

The present application claims priority under 35 U.S.C § 119 to Japanese Patent Application No. 2019-067291, filed on Mar. 29, 2019, which is hereby expressly incorporated by reference, in its entirety, into the present application.

BACKGROUND

Technical Field

The present disclosure relates to a control device, a medical imaging system, a control method, and a control program.

Related Art

In addition, an ultrasonography apparatus has been known which scans the breast of a subject with ultrasonic waves by moving an ultrasound probe along the breast to capture an ultrasound image of the breast.

In a case where an ultrasound image is captured, a depth to which capture of an ultrasound image with good accuracy is possible is determined according to an imaging condition such as frequency and a state of an object or the like. In a case where imaging is performed at a position deeper than the predetermined depth, the image quality of an ultrasound image is reduced or an imaging target portion is not imaged in some cases.

Therefore, JP2015-154916A discloses a display technique for clarifying an observation region up to an observable depth by an ultrasonography apparatus.

A technique of capturing an ultrasound image of the breast which is in a pressed state by a pressing member has been known. For example, a technique has been known which captures an ultrasound image of the breast in the pressed state by using a radiography apparatus that causes the breast to be in the pressed state by pressing the breast using the pressing member, irradiates the breast in the pressed state with radiation emitted from a radiation source, and detects the radiation transmitted through the breast with a radiation detector to capture a radiographic image.

The technique disclosed in JP2015-154916A is not sufficient for a case of capturing an ultrasound image of the breast in the pressed state, and the accuracy of the captured ultrasound image is reduced in some cases. In this way, in a case where the accuracy of the ultrasound image is reduced, since it is necessary to perform imaging again or it is not clear whether the reduction in accuracy is due to the setting of the ultrasonography apparatus or due to the performance of the ultrasonography apparatus, a technique of suppressing that an ultrasound image with reduced accuracy is captured is required.

SUMMARY

The present disclosure has been made in view of the above-described circumstances, and an object of the present disclosure is to provide a control device, a medical imaging system, a control method, and a control program which can suppress that an ultrasound image with reduced accuracy is captured.

In order to achieve the object, a control device according to a first aspect of the present disclosure comprises a breast thickness acquisition unit that acquires a thickness of a breast in a pressed state by a pressing member; a depth information acquisition unit that, in a case where an ultrasound image of the breast in the pressed state is captured, acquires depth information indicating a depth to which imaging by an ultrasonography apparatus which captures the ultrasound image is possible; a deriving unit that derives imaging information indicating whether or not capture of an ultrasound image having predetermined accuracy or higher is possible by the ultrasonography apparatus on the basis of the thickness of the breast acquired by the breast thickness acquisition unit and the depth information acquired by the depth information acquisition unit; and an output unit that outputs the imaging information derived by the deriving unit.

In a control device according to a second aspect of the present disclosure, in the control device according to the first aspect, the deriving unit derives the imaging information indicating that the capture of the ultrasound image does not satisfy the predetermined accuracy in a case where the thickness of the breast is thicker than a thickness corresponding to the depth indicated by the depth information.

In a control device according to a third aspect of the present disclosure, in the control device according to the first or second aspect, the deriving unit derives the imaging information indicating that the capture of the ultrasound image satisfies the predetermined accuracy in a case where the thickness of the breast is equal to or less than a thickness corresponding to the depth indicated by the depth information.

In a control device according to a fourth aspect of the present disclosure, in the control device according to any one of the first to third aspects, the depth information acquisition unit acquires the depth information of each of a plurality of the ultrasonography apparatuses, and the deriving unit derives the depth information for each of the plurality of ultrasonography apparatuses.

In a control device according to a fifth aspect of the present disclosure, in the control device according to the fourth aspect, the output unit outputs the imaging information only to the ultrasonography apparatus for which the imaging information indicating that the capture of the ultrasound image satisfies the predetermined accuracy is derived by the deriving unit, among the plurality of ultrasonography apparatuses.

In a control device according to a sixth aspect of the present disclosure, in the control device according to the fourth aspect, the output unit outputs the imaging information only to the ultrasonography apparatus for which the imaging information indicating that the capture of the ultrasound image does not satisfy the predetermined accuracy is derived by the deriving unit, among the plurality of ultrasonography apparatuses.

In a control device according to a seventh aspect of the present disclosure, in the control device according to any one of the first to sixth aspects, in a case where capture of a radiographic image of the breast by a radiography apparatus and the capture of the ultrasound image of the breast are continuously performed while the breast is in the pressed state, the deriving unit derives the imaging information before the capture of the radiographic image, and the output unit outputs the imaging information before the capture of the radiographic image.

In a control device according to an eighth aspect of the present disclosure, in the control device according to any one of the first to sixth aspects, in a case where capture of a radiographic image of the breast by a radiography apparatus and the capture of the ultrasound image of the breast are continuously performed while the breast is in the pressed state, the deriving unit derives the imaging information before the capture of the ultrasound image and after the capture of the radiographic image, and the output unit outputs the imaging information before the capture of the ultrasound image and after the capture of the radiographic image.

A control device according to a ninth aspect of the present disclosure, in the control device according to the eighth aspect, further comprises a radiographic image acquisition unit that acquires a plurality of reconstructed images obtained by reconstructing radiographic images captured at different irradiation angles, which are obtained in a case where the capture of the radiographic image is tomosynthesis imaging in which a radiation source irradiates the breast with radiation at the irradiation angles and a radiation detector captures the radiographic image at each of the irradiation angles; and a display control unit that performs control of causing a display unit to display the reconstructed image, information indicating a position of the breast in a height direction indicated by the reconstructed image, and the imaging information associated with the information indicating the position in the height direction.

In a control device according to a tenth aspect of the present disclosure, in the control device according to the ninth aspect, the display control unit performs control of causing the display unit to display the imaging information in association with the reconstructed image in a case where the display unit displays the reconstructed image within a range where the capture of the ultrasound image does not satisfy the predetermined accuracy on the basis of the imaging information.

A control device according to an eleventh aspect of the present disclosure, in the control device according to any one of the first to eighth aspects, further comprises a display control unit that performs control of causing a display unit to display the imaging information output by the output unit.

A control device according to a twelfth aspect of the present disclosure, in the control device according to any one of the first to eighth aspects, further comprises a display control unit that performs control of causing a display unit to display an image simulating the breast in the pressed state by adding information indicating at least one of a region where the predetermined accuracy is satisfied or a region where the predetermined accuracy is not satisfied to the image.

A control device according to a thirteenth aspect of the present disclosure, in the control device according to any one of the first to twelfth aspects, further comprises a pressing member information acquisition unit that acquires pressing member information indicating at least one of a thickness of the pressing member or hardness of the pressing member, in which the deriving unit derives the imaging information on the basis of the thickness of the breast, the depth information, and the pressing member information.

In a control device according to a fourteenth aspect of the present disclosure, in the control device according to any one of the first to thirteenth aspects, the deriving unit derives the imaging information on the basis of the thickness of the breast, the depth information, and mammary gland density of the breast.

A control device according to a fifteenth aspect of the present disclosure, in the control device according to the first aspects, further comprises a pressing member control unit that, in a case where a difference between the thickness of the breast and a thickness corresponding to the depth indicated by the depth information is within a movement allowable range of the pressing member, which presses the breast, in a height direction, on the basis of information indicating the movement allowable range performs control to move the pressing member to a position where the thickness of the breast in the pressed state becomes the depth indicated by the depth information.

In order to achieve the object, a medical imaging system according to a sixteenth aspect of the present disclosure comprises a mammography apparatus which includes a radiation source, a radiation detector, and a pressing member that presses a breast disposed between the radiation source and the radiation detector to a pressed state, and which causes the radiation detector to capture a radiographic image of the breast in the pressed state; an ultrasonography apparatus that captures an ultrasound image of the breast in the pressed state by the pressing member of the mammography apparatus; and the control device according to any one of the first to fifteenth aspects, which controls capture of the ultrasound image by the ultrasonography apparatus.

In order to achieve the object, a medical imaging system according to a seventeenth aspect of the present disclosure comprises a medical imaging apparatus which includes a radiation source, a radiation detector, and a pressing member that presses a breast disposed between the radiation source and the radiation detector to a pressed state, which causes the radiation detector to capture a radiographic image of the breast in the pressed state, and which captures an ultrasound image of the breast in the pressed state; and the control device according to any one of the first to fifteenth aspects, which controls the medical imaging apparatus.

In order to achieve the object, a control method according to an eighteenth aspect of the present disclosure is a control method for a computer to execute a process comprising acquiring a thickness of a breast in a pressed state by a pressing member; in a case where an ultrasound image of the breast in the pressed state is captured, acquiring depth information indicating a depth to which imaging by an ultrasonography apparatus which captures the ultrasound image is possible; deriving imaging information indicating whether or not capture of an ultrasound image having predetermined accuracy or higher is possible by the ultrasonography apparatus on the basis of the acquired thickness of the breast and the acquired depth information; and outputting the derived imaging information.

In order to achieve the object, a non-transitory computer readable medium storing a control program according to a nineteenth aspect of the present disclosure causes a computer to execute a process comprising acquiring a thickness of a breast in a pressed state by a pressing member; in a case where an ultrasound image of the breast in the pressed state is captured, acquiring depth information indicating a depth to which imaging by an ultrasonography apparatus which captures the ultrasound image is possible; deriving imaging information indicating whether or not capture of an ultrasound image having predetermined accuracy or higher is possible by the ultrasonography apparatus on the basis of the acquired thickness of the breast and the acquired depth information; and outputting the derived imaging information.

A control device according to an embodiment of the present disclosure is a control device including a processor and a memory, and the processor acquires a thickness of a breast in a pressed state by a pressing member; in a case where an ultrasound image of the breast in the pressed state is captured, acquires depth information indicating a depth to which imaging by an ultrasonography apparatus which captures the ultrasound image is possible; derives imaging information indicating whether or not capture of an ultrasound image having predetermined accuracy or higher is possible by the ultrasonography apparatus on the basis of the acquired thickness of the breast and the acquired depth information; and outputs the derived imaging information.

According to the present disclosure, it is possible to suppress that an ultrasound image with reduced accuracy is captured.

BRIEF DESCRIPTION OF THE DRAWINGS

FIG. 10 is a diagram illustrating an example of imaging information displayed on a display unit in the first embodiment.

FIG. 11A is a diagram illustrating an example of imaging information displayed on the display unit in Modification Example 1.

FIG. 11B is a diagram illustrating another example of imaging information displayed on the display unit in Modification Example 1.

FIG. 12 is a flowchart illustrating a part of an example of the flow of the control process in the console of Modification Example 2.

FIG. 13 is a configuration diagram schematically illustrating an example of the overall configuration of the medical imaging system of Modification Example 3.

FIG. 14 is a flowchart illustrating an example of the flow of the control process in the console of Modification Example 3.

DESCRIPTION OF EMBODIMENTS

Hereinafter, embodiments of the present disclosure will be described in detail with reference to the drawings. The embodiments do not limit the present disclosure. In the embodiments, a case in which an interested object of the present disclosure is a mammary gland will be described as an example.

First Embodiment

Figure 1:
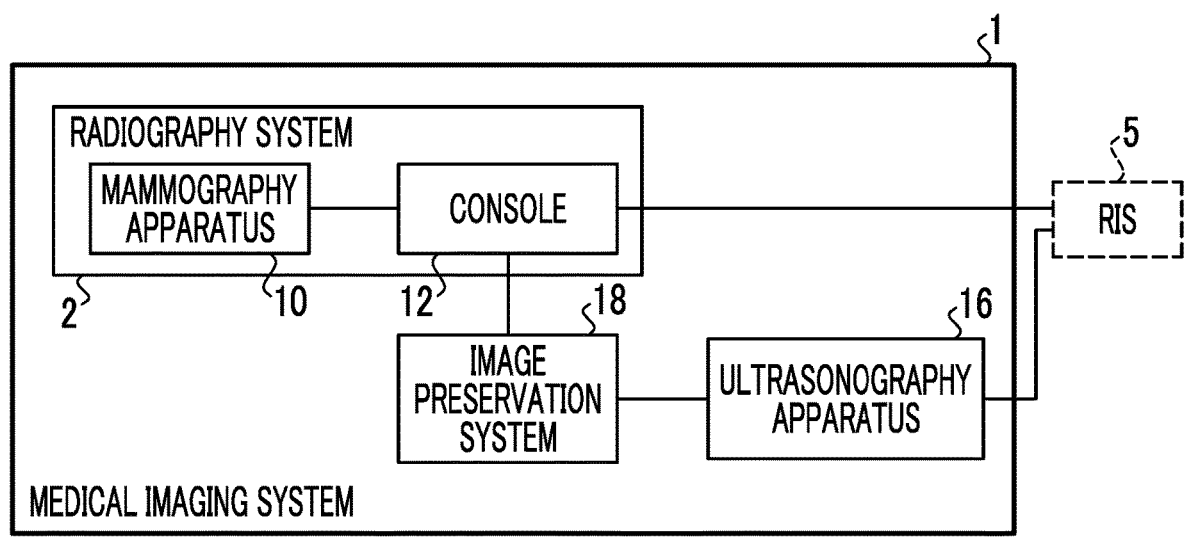
FIG. 1 is a configuration diagram schematically illustrating an example of the overall configuration of a medical imaging system of a first embodiment.

First, an example of the overall configuration of a medical imaging system of the embodiment will be described. FIG. 1 is a configuration diagram illustrating an example of the overall configuration of a medical imaging system 1 of the embodiment.

As illustrated in FIG. 1, the medical imaging system 1 of the embodiment comprises a radiography system 2, an ultrasonography apparatus 16, and an image preservation system 18.

Figure 2:
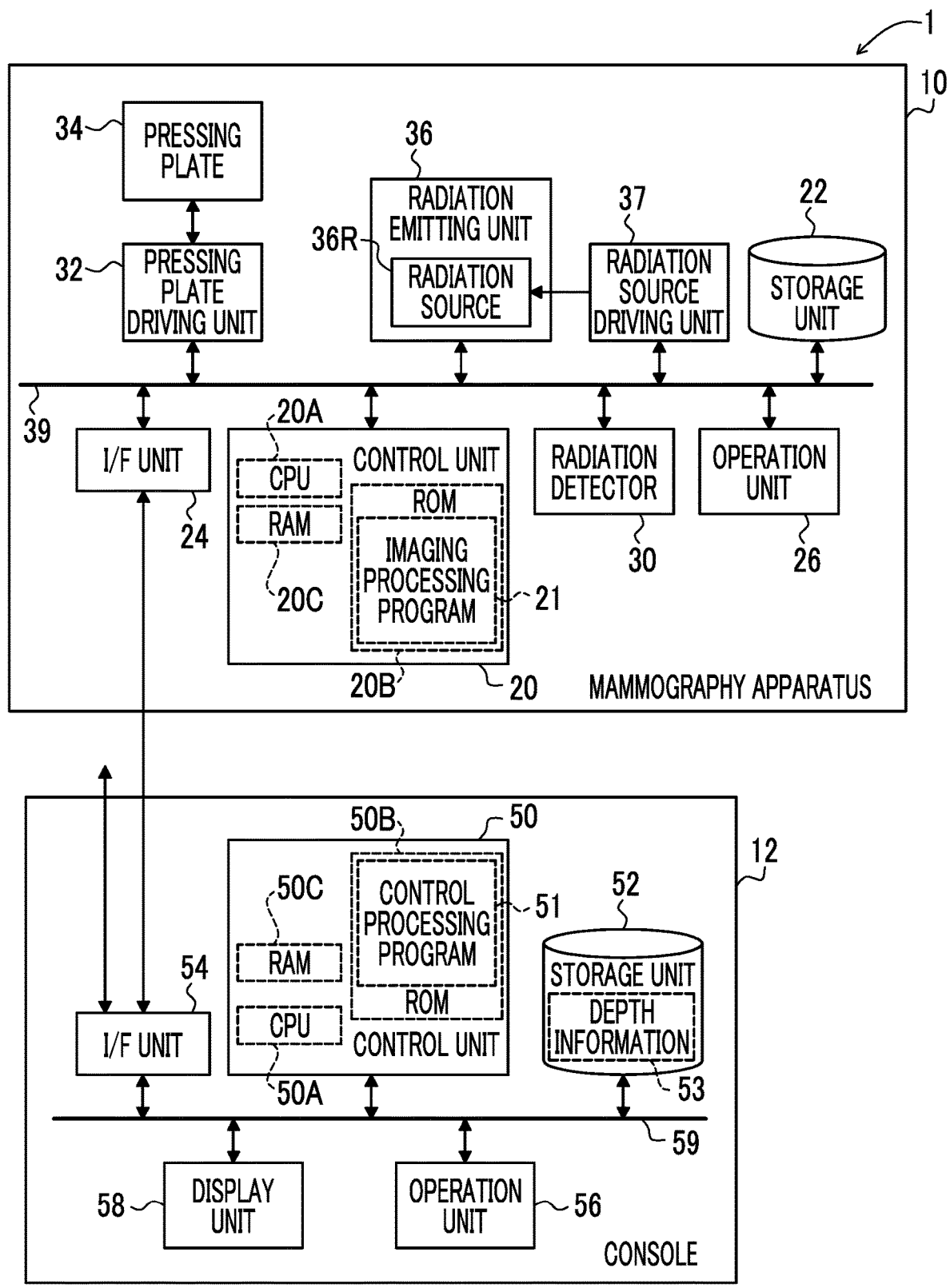
FIG. 2 is a block diagram illustrating an example of the configuration of a console and a mammography apparatus of the first embodiment.
Figure 3:
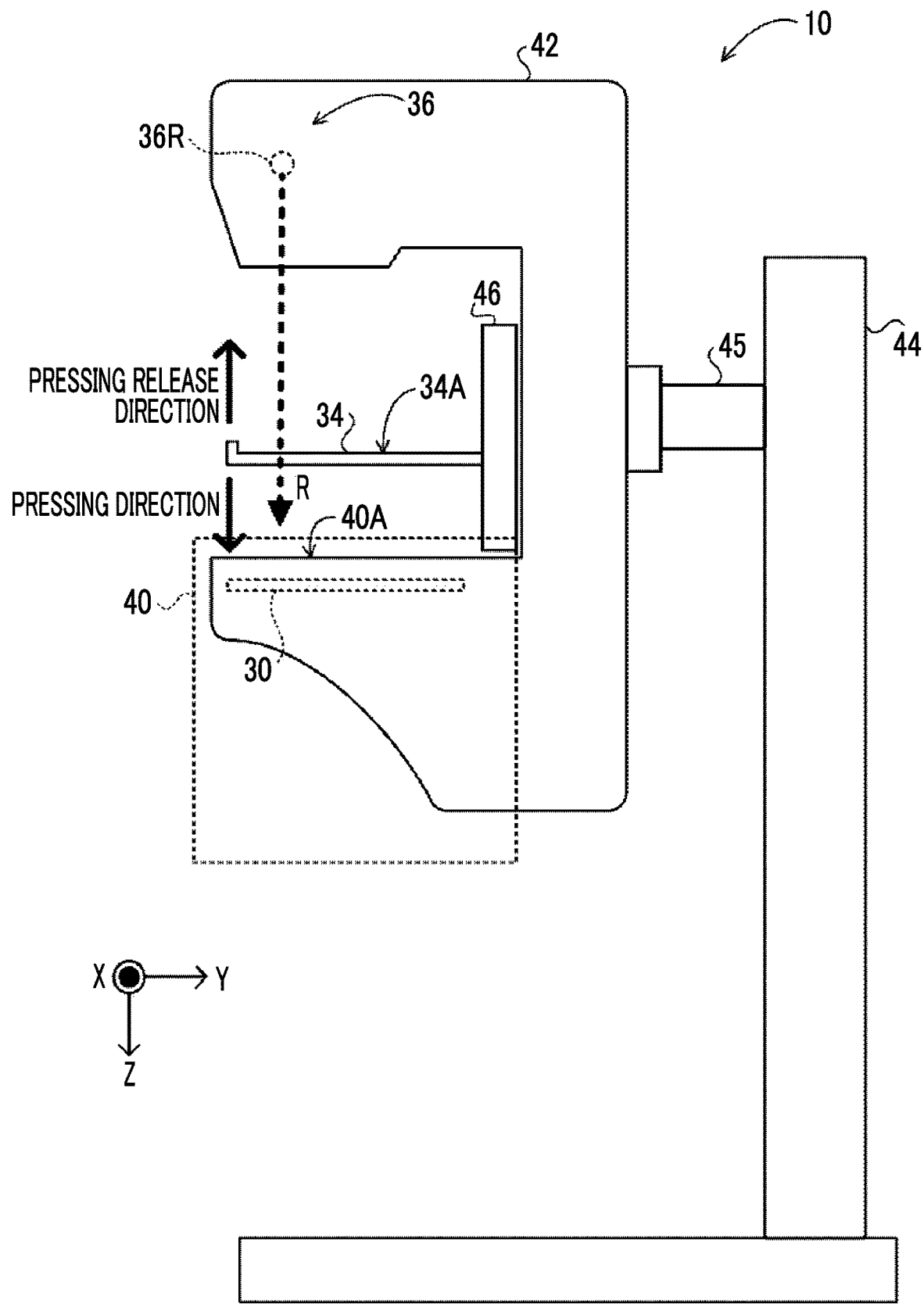
FIG. 3 is a side view illustrating an example of the appearance of the mammography apparatus of the first embodiment.

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the appearance of the mammography apparatus 10 of the embodiment.

The mammography apparatus 10 of the embodiment is an apparatus that irradiates the breast of a subject as an object with radiation R (for example, X-rays) to capture a radiographic image of the breast. In addition, the mammography apparatus 10 may be an apparatus that images the breast of the subject not only in a state in which the subject is standing (standing position state) but also in a state in which the subject sits on a chair (including a wheelchair) or the like (sitting position state).

As illustrated in FIG. 2, the mammography apparatus 10 of the embodiment comprises a control unit 20, a storage unit 22, an interface (I/F) unit 24, an operation unit 26, a radiation detector 30, a pressing plate driving unit 32, a pressing plate 34, a radiation emitting unit 36, and a radiation source driving unit 37. The control unit 20, the storage unit 22, the I/F unit 24, the operation unit 26, the radiation detector 30, the pressing plate driving unit 32, the radiation emitting unit 36, and the radiation source driving unit 37 are connected to each other through a bus 39, such as a system bus or a control bus, so as to be able to transmit and receive various kinds of information.

The control unit 20 of the embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including an imaging processing program 21 which is executed by the CPU 20A and performs control relating to the capture of a radiographic image are stored in the ROM 20B in advance. The RAM 20C temporarily stores various kinds of data.

The radiation detector 30 detects the radiation R transmitted through the breast which is the object. As illustrated in FIG. 3, the radiation detector 30 is provided in an imaging table 40. In the mammography apparatus 10 of the embodiment, in a case in which imaging is performed, the breast of the subject is positioned on an imaging surface 40A of the imaging table 40 by a user such as a doctor or a radiology technician. The imaging surface 40A or the like with which the breast of the subject comes into contact is made of, for example, carbon in terms of the transmittance and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 of the embodiment is not particularly limited. For example, the radiation detector 30 may be an indirect-conversion-type radiation detector that converts the radiation R into light and converts the converted light into charge, or may be a direct-conversion-type radiation detector that directly converts the radiation R into charge.

For example, the image data of the radiographic image captured by the radiation detector 30 and various other kinds of information are stored in the storage unit 22. Specific examples of the storage unit 22 include a hard disk drive (HDD) and a solid state drive (SSD). The I/F unit 24 performs communication of various kinds of information with the console 12 through wireless communication or wired communication. In the mammography apparatus 10, the image data of the radiographic image captured by the radiation detector 30 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a pressing unit 46. In addition, as illustrated in FIG. 3, the mammography apparatus 10 of the embodiment comprises the arm portion 42, a base 44, and a shaft portion 45. The arm portion 42 is held by the base 44 so as to be movable in a vertical direction (Z-axis direction). The shaft portion 45 connects the arm portion 42 to the base 44. The radiation source driving unit 37 can relatively rotate the arm portion 42 with respect to the base 44, using the shaft portion 45 as a rotation axis.

Figures 4, 5:
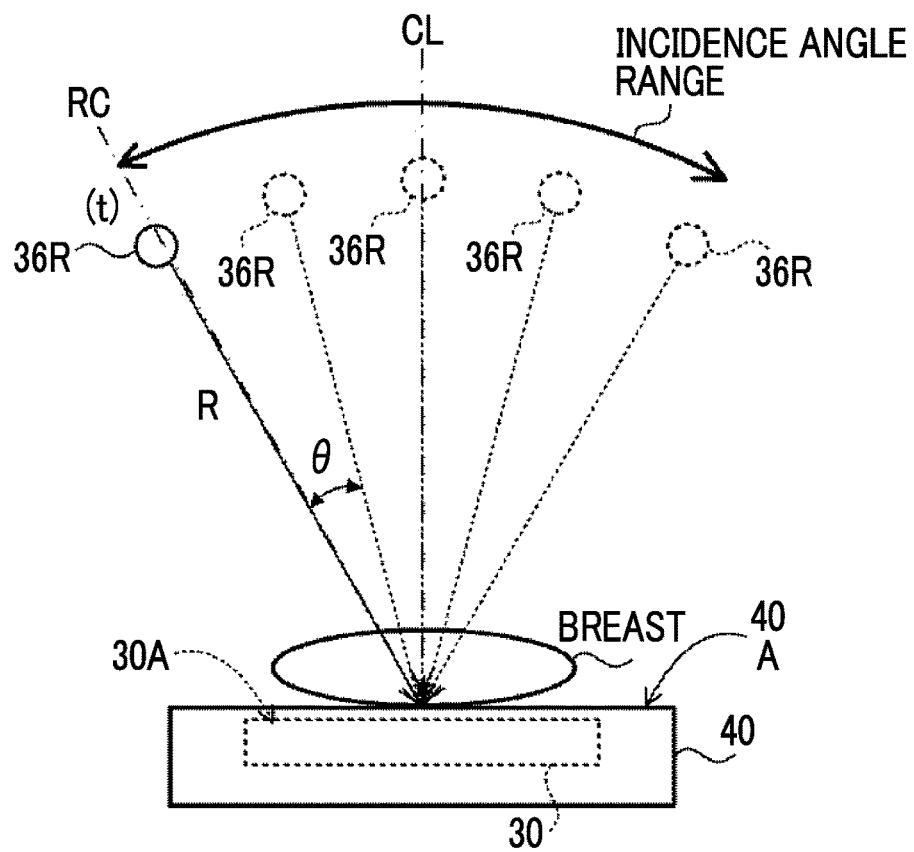
FIG. 4 is a diagram describing tomosynthesis imaging by the mammography apparatus of the first embodiment.
FIG. 5 is a diagram illustrating an example of depth information of the first embodiment.

In a case in which the mammography apparatus 10 performs tomosynthesis imaging, with the rotation of the arm portion 42, the radiation source 36R of the radiation emitting unit 36 is continuously moved to each of a plurality of irradiation positions with different irradiation angles (projection angles) by the radiation source driving unit 37. In the embodiment, as illustrated in FIG. 4, the radiation source 36R is moved to irradiation positions t (t=0, 1, T; T=5 in FIG. 4) with irradiation angles which are different by a predetermined angle θ, in other words, positions where the incidence angles of the radiation R with respect to a detection surface 30A of the radiation detector 30 are different. At each irradiation position, the radiation R is emitted from the radiation source 36R in response to an instruction from the console 12, and the radiation detector 30 captures a radiographic image. In case of performing tomosynthesis imaging which captures a projection image at each irradiation position t by moving the radiation source 36R to each of the irradiation positions t, the radiography system 2 obtains T projection images. In the embodiment, an aspect in which the radiation emitting unit 36 is moved to move the radiation source 36R to the irradiation position t has been described. However, the present disclosure is not limited to the embodiment. For example, an aspect in which the mammography apparatus 10 comprises a plurality of radiation sources 36R corresponding to each irradiation position t may be adopted.

As illustrated in FIG. 3, the pressing plate 34 is provided to the pressing unit 46. Each of the pressing unit 46 and the arm portion 42 can be relatively rotated with respect to the base 44, using the shaft portion 45 as a rotation axis. In the embodiment, gears (not illustrated) are provided in each of the shaft portion 45, the arm portion 42, and the pressing unit 46. The gears are switched between an engaged state and a disengaged state to connect each of the arm portion 42 and the pressing unit 46 to the shaft portion 45. One or both of the arm portion 42 and the pressing unit 46 connected to the shaft portion 45 are rotated integrally with the shaft portion 45.

The pressing plate 34 of the embodiment is a plate-shaped pressing member, and is moved in the vertical direction (Z-axis direction) by the pressing plate driving unit 32 to press the breast of the subject against the imaging table 40. As illustrated in FIG. 3, for the movement direction of the pressing plate 34, a direction in which the breast is pressed, that is, a direction approaching the imaging surface 40A is referred to as a "pressing direction", and a direction in which the pressing against the breast is released, that is, a direction approaching the radiation emitting unit 36 is referred to as a "pressing release direction". The pressing plate 34 of the embodiment is an example of the pressing member of the present disclosure.

It is preferable that the pressing plate 34 is optically transparent in order to check the positioning or the pressed state in the pressing of the breast, and further, the pressing plate 34 is made of a material having high transmittance for the radiation R. It is desirable that the pressing plate 34 is made of a material that facilitates the transmission of ultrasonic waves from an ultrasound probe 65 (refer to FIG. 7, which will be described in detail below) of the ultrasonography apparatus 16. Examples of the material forming the pressing plate 34 include resins such as polymethylpentene, silicone rubber, polycarbonate, acrylic, and polyethylene terephthalate. In particular, polymethylpentene is suitable as the material forming the pressing plate 34 since polymethylpentene has low rigidity, high elasticity, and high flexibility, and has suitable values for acoustic impedance that affects the reflectance of ultrasonic waves and an attenuation coefficient that affects the attenuation of ultrasonic waves. The member constituting the pressing plate 34 is not limited to the embodiment. For example, the member constituting the pressing plate 34 may be a film-like member.

The pressing plate 34 is not limited to a pressing plate that presses the entire breast, and the pressing plate 34 may be a pressing plate that presses a part of the breast. In other words, the pressing plate 34 may be smaller than the breast. For example, a pressing plate used in so-called spot imaging which captures a radiographic image of only a region where a lesion is present is known as the pressing plate 34.

The console 12 of the embodiment has a function of controlling the mammography apparatus 10 using, for example, an imaging order and various kinds of information acquired from a radiology information system (RIS) 5 through a wireless communication local area network (LAN) and an instruction or the like input by the user through an operation unit 56.

The console 12 of the embodiment is a server computer, for example. As illustrated in FIG. 2, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, so as to be able to transmit and receive various kinds of information.

The control unit 50 of the embodiment controls the overall operation of the console 12. The control unit 50 comprises a CPU 50A, a ROM 50B, and a RAM 50C. Various programs including a control processing program 51, which will be described below, executed by the CPU 50A are stored in the ROM 50B in advance. The RAM 50C temporarily stores various kinds of data.

The image data of the radiographic image captured by the mammography apparatus 10 and various other kinds of information are stored in the storage unit 52. Depth information 53 of which an example is illustrated in FIG. 5 is stored in the storage unit 52 of the embodiment. The ultrasonography apparatus 16 has a predetermined depth to which imaging with higher accuracy than predetermined accuracy is possible. In the embodiment, a limit depth to which imaging with predetermined accuracy or higher is possible is referred to as a "limit depth". As the limit depth, for example, penetration depth is exemplified. The predetermined accuracy refers to accuracy required for diagnosis (examination), such as accuracy where a desired site of interest such as a mass or a calcification can be properly observed using an ultrasound image.

For example, as the frequency of ultrasonic waves is increased, the wavelength of the ultrasonic waves becomes shorter, and the amount of attenuation in biological tissues is increased. Therefore, it is known that the limit depth becomes shallow (short). The limit depth differs depending on the ultrasonography apparatus 16, for example, the ultrasound probe 65 (refer to FIG. 7) to be used. The depth information 53 is information in which information indicating the ultrasonography apparatus 16 and the limit depth corresponding to the ultrasonography apparatus 16 are associated with each other. In the depth information 53 illustrated in FIG. 5, apparatus names such as an "apparatus A", an "apparatus B", an "apparatus C", and an "apparatus D" are used as the information indicating the ultrasonography apparatus 16. However, the present disclosure is not limited thereto, and for example, identification information such as an identification (ID) indicating the ultrasonography apparatus 16 may be used. The depth information 53 is not limited thereto, and for example, information indicating the ultrasound probe 65 may be used instead of the information indicating the ultrasonography apparatus 16. Specific examples of the storage unit 52 include an HDD, an SSD, and the like.

The operation unit 56 is used by the user to input, for example, various kinds of information or instructions relating to the capture of a radiographic image and including an instruction to emit the radiation R. Therefore, the operation unit 56 of the embodiment includes at least an irradiation instruction button that is pressed by the user to input an instruction to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 performs communication of various kinds of information between the mammography apparatus 10, the RIS 5, and the image preservation system 18 using wireless communication or wired communication. In the radiography system 2 of the embodiment, the console 12 receives the image data of the radiographic image captured by the mammography apparatus 10 from the mammography apparatus 10 through the I/F unit 54, using wireless communication or wired communication.

Figure 6:
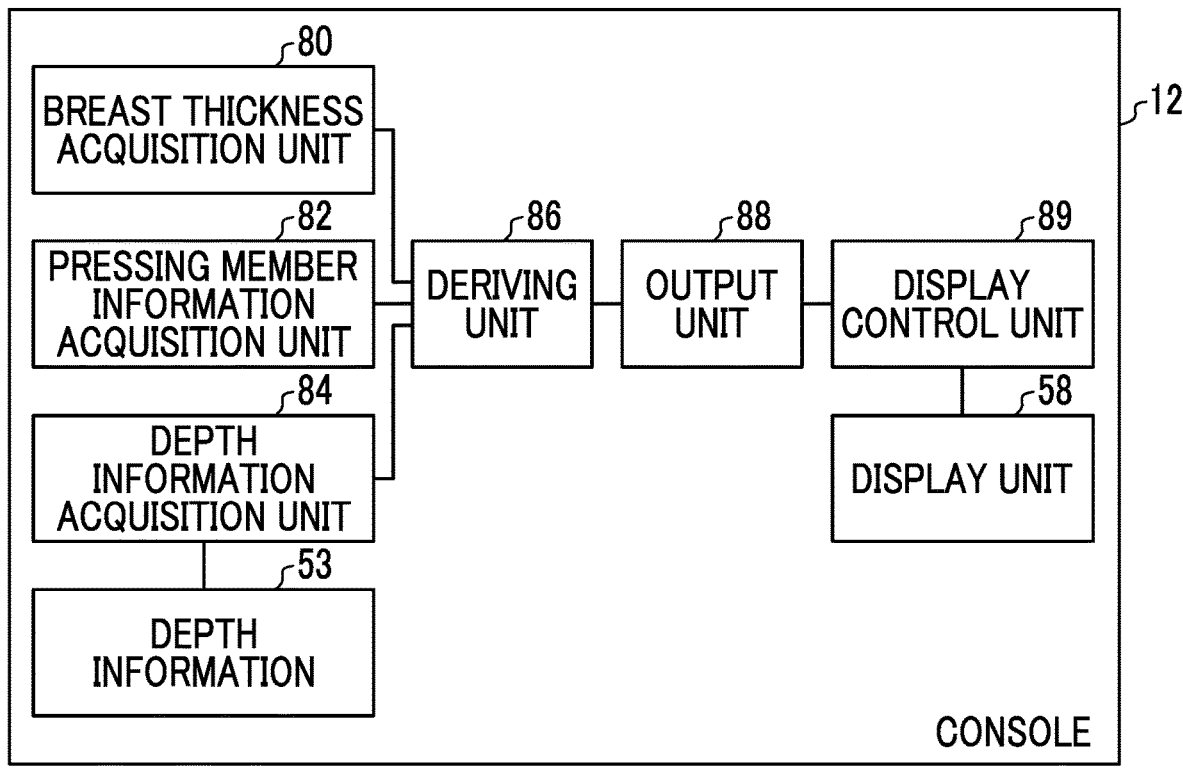
FIG. 6 is a functional block diagram illustrating an example of the function of the console of the first embodiment.

FIG. 6 is a functional block diagram illustrating an example of the configuration of the console 12 of the embodiment. As illustrated in FIG. 6, the console 12 of the embodiment comprises a breast thickness acquisition unit 80, a pressing member information acquisition unit 82, a depth information acquisition unit 84, a deriving unit 86, an output unit 88, and a display control unit 89. For example, in the console 12 of the embodiment, the CPU 50A of the control unit 50 executes the control processing program 51 stored in the ROM 50B so that the control unit 50 functions as the breast thickness acquisition unit 80, the pressing member information acquisition unit 82, the depth information acquisition unit 84, the deriving unit 86, the output unit 88, and the display control unit 89.

The breast thickness acquisition unit 80 acquires the thickness of the breast which is pressed by the pressing plate 34. The thickness of the breast in the pressed state by the pressing plate 34 corresponds to the distance between the imaging table 40 and the pressing plate 34. Therefore, in the embodiment, for example, the distance between the imaging table 40 and the pressing plate 34 is used as the thickness of the breast. Specifically, in the radiography system 2 of the embodiment, the control unit 20 of the mammography apparatus 10 derives the thickness of the breast according to a movement amount of the pressing plate 34 from the predetermined initial position by the pressing plate driving unit 32 in order to press the breast, and the position of the imaging table 40. The breast thickness acquisition unit 80 acquires information indicating the derived thickness of the breast from the mammography apparatus 10.

The method of deriving the thickness of the breast is not limited to the embodiment. For example, the breast thickness acquisition unit 80 may acquire the information indicating the movement amount of the pressing plate 34 and the position of the imaging table 40 from the mammography apparatus 10, and the breast thickness acquisition unit 80 may derive the thickness of the breast on the basis of the acquired information. In addition, for example, a sensor for distance measurement such as an ultrasonic sensor may be provided to the pressing plate 34 or the imaging table 40, and a method of deriving the distance between the imaging table 40 and the pressing plate 34 which is measured by the sensor for distance measurement as the thickness of the breast may be used. Further, for example, the breast in the pressed state by the pressing plate 34 may be imaged by the imaging device, and a method of deriving the distance between the imaging table 40 and the pressing plate 34 as the thickness of the breast on the basis of the captured image may be used.

The pressing member information acquisition unit 82 acquires pressing member information relating to the pressing plate 34 and affecting the limit depth from the mammography apparatus 10. For example, in a case where an ultrasound image is captured, since the ultrasound probe 65 abuts against an upper surface 34A of the pressing plate 34 to output ultrasonic waves, a thickness obtained by adding the thickness of the pressing plate 34 to the thickness of the breast may become an imaging distance in some cases. In this case, since it is preferable to consider the thickness of the pressing plate 34, it is preferable to acquire the thickness of the pressing plate 34 as the pressing member information. For example, since the ultrasonic waves are attenuated by being transmitted through the pressing plate 34, it is preferable to acquire the hardness of the pressing plate 34, the thickness of the pressing plate 34, and the like which are factors affecting the attenuation of ultrasonic waves, as the pressing member information. Further, the present disclosure is not limited thereto, and for example, the material or the like of the pressing plate 34 may be acquired as the pressing member information.

The method for the pressing member information acquisition unit 82 to acquire the pressing member information is not particularly limited, and for example, in a case where the mammography apparatus 10 itself includes the pressing member information, the pressing member information acquisition unit 82 may acquire the pressing member information from the mammography apparatus 10. For example, an aspect in which the pressing member information acquisition unit 82 acquires identification information for identifying the pressing plate 34 from the mammography apparatus 10 and acquires the pressing member information associated with the acquired identification information from external devices may be adopted.

The depth information acquisition unit 84 acquires the limit depth corresponding to the ultrasonography apparatus 16 used in the capture of an ultrasound image, from the depth information 53. As an example, in a case where the user inputs the information indicating the ultrasonography apparatus 16 through the operation unit 56, the depth information acquisition unit 84 of the embodiment acquires the limit depth corresponding to the input information indicating the ultrasonography apparatus 16 from the depth information 53. The method for the depth information acquisition unit 84 to acquire the limit depth is not limited to the embodiment. For example, in a case where the ultrasonography apparatus 16 itself grasps the limit depth, the depth information acquisition unit 84 may acquire the limit depth from the ultrasonography apparatus 16.

The deriving unit 86 derives imaging information (described in detail below) indicating whether or not it is possible for the ultrasonography apparatus 16 to capture an ultrasound image with predetermined accuracy or higher, on the basis of the thickness of the breast in the pressed state acquired by the breast thickness acquisition unit 80, the pressing member information acquired by the pressing member information acquisition unit 82, and the limit depth acquired by the depth information acquisition unit 84.

The output unit 88 outputs the imaging information derived by the deriving unit 86. As an example, the output unit 88 of the embodiment outputs the imaging information to the display control unit 89, but the output destination to which the output unit 88 outputs the imaging information is not limited thereto. For example, an aspect in which the output destination is the ultrasonography apparatus 16 may be adopted. Further, an aspect in which the output destination is another external device such as a mobile terminal device owned by the user may be adopted.

The display control unit 89 performs control of causing the display unit 58 to display the imaging information.

Figure 7:
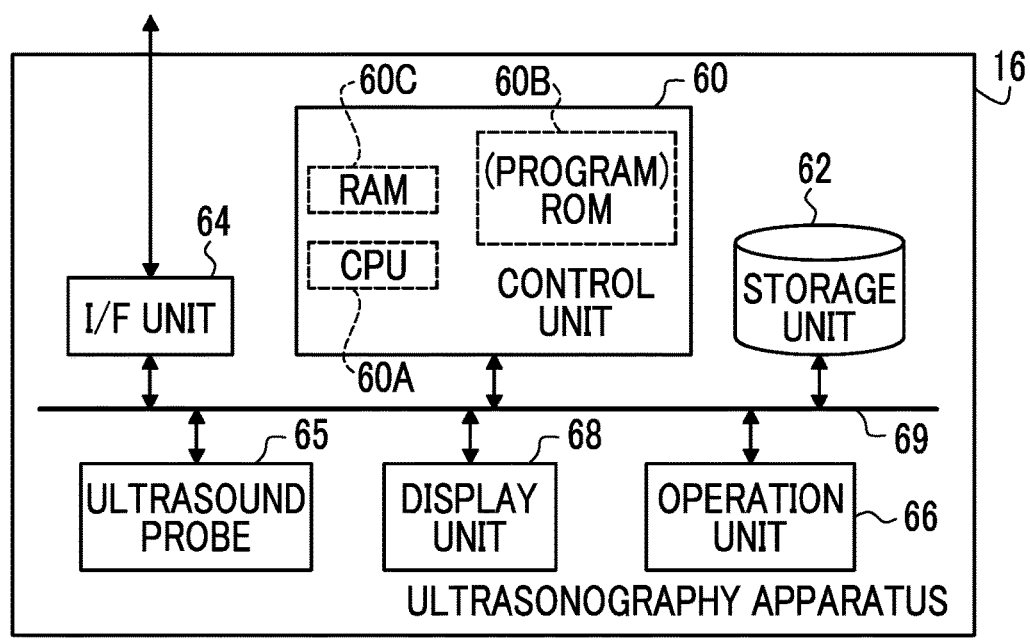
FIG. 7 is a block diagram illustrating an example of the configuration of an ultrasonography apparatus of the first embodiment.

Next, the configuration of the ultrasonography apparatus 16 will be described. FIG. 7 is a block diagram illustrating an example of the configuration of the ultrasonography apparatus 16. The ultrasonography apparatus 16 is an apparatus used by the user to capture an ultrasound image of the breast of the subject as the object and is a so-called handheld ultrasonography apparatus.

As illustrated in FIG. 7, the ultrasonography apparatus 16 comprises a control unit 60, a storage unit 62, an I/F unit 64, the ultrasound probe 65, an operation unit 66, and a display unit 68. The control unit 60, the storage unit 62, the I/F unit 64, the ultrasound probe 65, the operation unit 66, and the display unit 68 are connected to each other through a bus 69, such as a system bus or a control bus, so as to be able to transmit and receive various kinds of information.

The control unit 60 of the embodiment controls the overall operation of the ultrasonography apparatus 16. The control unit 60 comprises a CPU 60A, a ROM 60B, and a RAM 60C. Various programs executed by the CPU 60A are stored in the ROM 60B in advance. The RAM 60C temporarily stores various kinds of data.

The image data of the captured ultrasound image and various other kinds of information are stored in the storage unit 62. Specific examples of the storage unit 62 include an HDD, an SSD, and the like.

The ultrasound probe 65 is moved along the upper surface 34A (refer to FIG. 3, a surface opposite to the surface that comes into contact with the breast of the subject) of the pressing plate 34 by the user and scans the breast with ultrasonic waves to acquire an ultrasound image of the breast. Specifically, in a case in which ultrasonography is performed, the ultrasound probe 65 is moved by the user along the upper surface 34A of the pressing plate 34 in a state in which an acoustic matching member (not illustrated), such as echo jelly, is applied onto the upper surface 34A of the pressing plate 34.

The ultrasound probe 65 comprises a plurality of ultrasound transducers (not illustrated) which are one-dimensionally or two-dimensionally arranged. Each of the ultrasound transducers transmits ultrasonic waves on the basis of an applied drive signal, receives ultrasound echoes, and outputs a received signal.

For example, each of the plurality of ultrasound transducers is a transducer configured by forming electrodes at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are combined to form an ultrasound beam. Each transducer receives the propagated ultrasonic waves and is then expanded and contracted to generate an electrical signal. The electrical signal is output as an ultrasound received signal and is input to the main body (not illustrated) of the ultrasonography apparatus 16 through a cable (not illustrated).

The operation unit 66 is used by the user to input, for example, various kinds of information or instructions relating to the capture of an ultrasound image. The operation unit 66 is not particularly limited. Examples of the operation unit 66 include various switches, a touch panel, a touch pen, and a mouse. The display unit 68 displays, for example, various kinds of information or an ultrasound image corresponding to the received signal from the ultrasound probe 65. In addition, the operation unit 66 and the display unit 68 may be integrated into a touch panel display.

The I/F unit 64 performs communication of various kinds of information between the RIS 5 and the image preservation system 18 using wireless communication or wired communication. The image data of the ultrasound image captured by the ultrasonography apparatus 16 is transmitted to the image preservation system 18 through the I/F unit 64 by wireless communication or wired communication.

Figure 8:
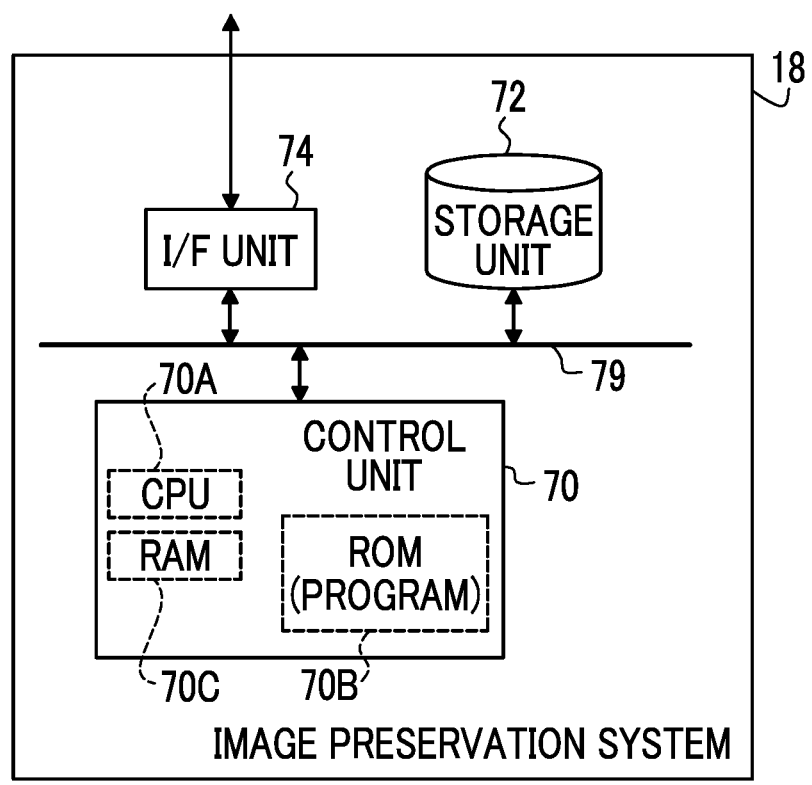
FIG. 8 is a block diagram illustrating an example of the configuration of an image preservation system of the first embodiment.

Next, the configuration of the image preservation system 18 will be described. FIG. 8 is a block diagram illustrating an example of the configuration of the image preservation system 18. The image preservation system 18 is a system that preserves the image data of the radiographic image captured by the radiography system 2 and the image data of the ultrasound image captured by the ultrasonography apparatus 16. The image preservation system 18 extracts an image corresponding to a request from, for example, the console 12, the ultrasonography apparatus 16, and other reading devices (not illustrated) from the preserved radiographic images and ultrasound images, and transmits the extracted image to the apparatus which is the request source. A specific example of the image preservation system 18 is picture archiving and communication systems (PACS).

As illustrated in FIG. 8, the image preservation system 18 comprises a control unit 70, a storage unit 72, and an I/F unit 74. The control unit 70, the storage unit 72, and the I/F unit 74 are connected to each other through a bus 79, such as a system bus or a control bus, so as to be able to transmit and receive various kinds of information.

The control unit 70 of the embodiment controls the overall operation of the image preservation system 18. The control unit 70 comprises a CPU 70A, a ROM 70B, and a RAM 70C. Various programs executed by the CPU 70A are stored in the ROM 70B in advance. The RAM 70C temporarily stores various kinds of data.

The storage unit 72 is a so-called database that stores each of the image data of the radiographic image and the image data of the ultrasound image in an association manner with, for example, an imaging order or information relating to the subject.

The I/F unit 74 has a function of performing communication of various kinds of information with the console 12 and the ultrasonography apparatus 16 using wireless communication or wired communication.

Next, the operation of the console 12 of the embodiment will be described with reference to the drawings.

Figure 9:
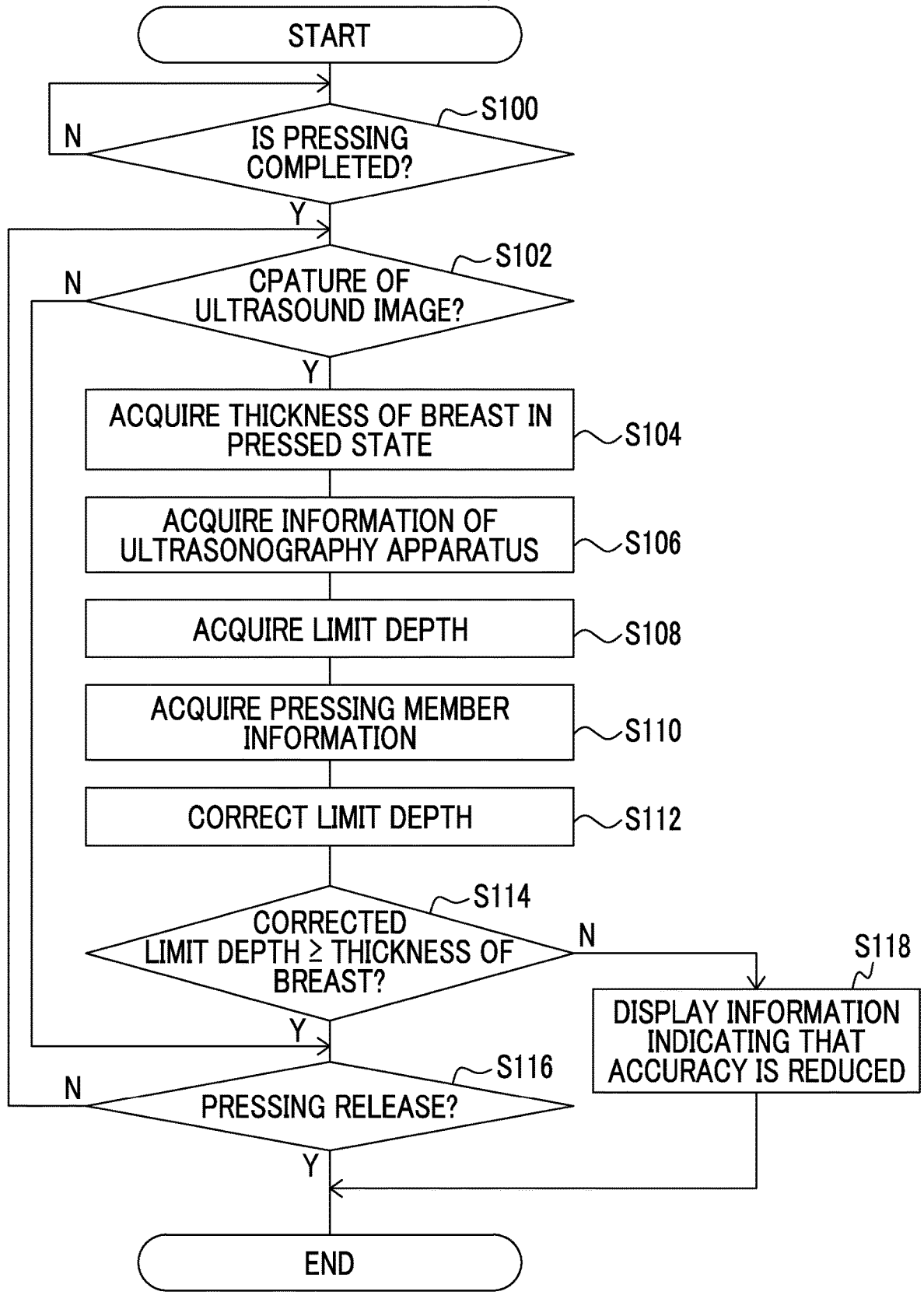
FIG. 9 is a flowchart illustrating an example of the flow of a control process in the console of the first embodiment.

For example, in a case in which the console 12 of the embodiment receives an imaging start instruction according to an imaging order which is instructed from the user through the operation unit 56, the CPU 50A of the control unit 50 executes the control processing program 51 stored in the ROM 50B to execute a control process of which an example is illustrated in FIG. 9. FIG. 9 is a flowchart illustrating an example of the flow of the control operation in the console 12 of the embodiment.

First, in step S100, the deriving unit 86 determines whether or not the pressing of the breast by the pressing plate 34 in the mammography apparatus 10 is completed.

In a case in which the mammography apparatus 10 of the embodiment captures a radiographic image, first, the user positions the breast of the subject on the imaging surface 40A of the imaging table 40 of the mammography apparatus 10. In a case in which the positioning is completed, the user inputs a pressing instruction through the operation unit 26 of the mammography apparatus 10.

The pressing of the breast by the pressing plate 34 makes it possible to develop the overlap between the mammary gland tissues and to easily determine whether a lesion is a benign lesion or a malignant lesion. In addition, since the breast is fixed to the imaging table 40 by being pressed by the pressing plate 34, the body movement of the subject is suppressed, and therefore, it is possible to suppress the blurring of a radiographic image caused by the body movement. Further, since the breast is pressed by the pressing plate 34, the thickness of the breast is reduced, and therefore, it is possible to reduce the amount of radiation emitted to the breast.

As an example, in the radiography system 2 of the embodiment, in a case where the fixing of the breast by the pressing plate 34 is completed, the user inputs information indicating that the pressing is completed, through the operation unit 26 of the mammography apparatus 10 or the operation unit 56 of the console 12.

Until the information indicating that the pressing is completed is input, the determination of step S100 is negative. On the other hand, in a case where the information indicating that the pressing is completed is input, the determination of step S100 is affirmative, and the process proceeds to step S102.

In step S102, the deriving unit 86 determines whether to capture an ultrasound image. As an example, in a case where an instruction to capture both a radiographic image and an ultrasound image is included in the imaging order or the user inputs an instruction to capture an ultrasound image through the operation unit 56, the deriving unit 86 of the embodiment determines to capture an ultrasound image. In a case in which an ultrasound image is not captured, the determination of step S102 is negative, and the process proceeds to step S116. On the other hand, in a case where an ultrasound image is captured, the determination of step S102 is affirmative, and the process proceeds to step S104.

In step S104, the breast thickness acquisition unit 80 acquires the thickness of the breast which is in the pressed state by the pressing plate 34 of the mammography apparatus 10, as described above.

In step S106, the depth information acquisition unit 84 acquires information indicating the ultrasonography apparatus 16 which is input by the user, as described above.

In step S108, the depth information acquisition unit 84 acquires the limit depth corresponding to the acquired information indicating the ultrasonography apparatus 16, from the depth information 53.

In step S110, the pressing member information acquisition unit 82 acquires the pressing member information relating to the pressing plate 34 as described above.

In step S112, the deriving unit 86 corrects the limit depth acquired in step S108 using the pressing member information acquired in step S110. The method for the deriving unit 86 to correct the limit depth using the pressing member information is not particularly limited. For example, in the embodiment, a correction coefficient (not illustrated) used for correcting the limit depth according to the pressing member information is stored in the storage unit 52 in advance, and the deriving unit 86 acquires the correction coefficient according to the pressing member information from the storage unit 52 and corrects the limit depth using the acquired correction coefficient.

For example, unlike the embodiment, an aspect in which a correspondence relationship between the information indicating the pressing plate 34 and the correction coefficient of the limit depth is obtained, the information indicating the pressing plate 34 is acquired from the mammography apparatus 10, and the deriving unit 86 acquires a limit depth correction coefficient on the basis of the acquired information indicating the pressing plate 34 and the correspondence relationship may be adopted.

In the embodiment, only the limit depth is corrected, but an aspect in which the thickness of the breast is corrected may be adopted. For example, in a case where the thickness of the pressing plate 34 is acquired as the pressing member information, the thickness of the breast may be corrected by adding the thickness of the pressing plate 34 to the thickness of the breast acquired in step S104.

In step S114, the deriving unit 86 determines whether or not the corrected limit depth is equal to or greater than the thickness of the breast (the corrected limit depth≥the thickness of the breast), and outputs the imaging information according to the determination result. In a case where the corrected limit depth is not equal to or greater than the thickness of the breast, in other words, in a case where the corrected limit depth is less than the thickness of the breast, the determination of step S114 is negative, and the process proceeds to step S118.

In step S118, the display control unit 89 performs control of causing the display unit 58 to display information indicating that the imaging accuracy for the ultrasound image is reduced, on the basis of the imaging information. Specifically, in the embodiment, in a case where the corrected limit depth is less than the thickness of the breast, the imaging information including the information indicating that the imaging accuracy is reduced is derived by the deriving unit 86 and is output to the output unit 88. The display control unit 89 performs control of causing the display unit 58 to display the information indicating that the imaging accuracy for the ultrasound image is reduced, according to the imaging information output from the output unit 88.

FIG. 10 illustrates an example of imaging information 90 displayed on the display unit 58 under the control of the display control unit 89. FIG. 10 illustrates an example of the imaging information 90 corresponding to a case where the ultrasonography apparatus 16 is the "apparatus B" in the depth information 53 illustrated in FIG. 5. The imaging information 90 illustrated in FIG. 10 indicates the thickness (30 mm) of the breast in the pressed state, the information indicating the ultrasonography apparatus 16 (apparatus B), an imaging possible range (20 to 30 mm) and an imaging impossible range (0 to 20 mm).

The "imaging possible range" refers to a range equal to or less than the limit depth, more specifically, a range not exceeding the limit depth corrected in step S112, and is indicated by the height of the breast. In case of the imaging information 90 illustrated in FIG. 10, a range of 20 mm or more and 30 mm or less from the imaging surface 40A of the imaging table 40 is the imaging possible range. Specifically, the breast within 10 mm from the lower surface of the pressing plate 34 becomes the imaging possible range.

Further, the "imaging impossible range" refers to a range exceeding the limit depth, more specifically, a range exceeding the limit depth corrected in step S112, and is indicated by the height of the breast. In case of the imaging information 90 illustrated in FIG. 10, a range of 0 mm or more and less than 20 mm from the imaging surface 40A of the imaging table 40 is the imaging impossible range. Even in the imaging impossible range exceeding the limit depth, the capture of the ultrasound image is not always impossible, and a case where the capture of the ultrasound image is possible but the accuracy of the captured ultrasound image is not equal to or greater than the predetermined accuracy is included.

In step S118, the control of displaying the imaging information 90 by the display control unit 89 is ended, the present control process is ended.

On the other hand, in a case where the corrected limit depth is equal to or greater than the thickness of the breast, the determination of step S114 is affirmative, and the process proceeds to step S116.

In the embodiment, in a case where the imaging information 90 is not displayed on the display unit 58 of the console 12, since the capture of an ultrasound image with predetermined accuracy or higher is possible, the capture of an ultrasound image by the ultrasonography apparatus 16 is performed. In addition, the capture of a radiographic image by the mammography apparatus 10 is performed.

As an example, in the embodiment, in a case where both a radiographic image and an ultrasound image are captured, a radiographic image is captured first. In a case where a radiographic image is captured, the user presses an irradiation instruction button included in the operation unit 56 of the console 12 to input an instruction to emit the radiation R. In a case in which the irradiation instruction is input, the control unit 20 of the mammography apparatus 10 performs control such that the radiation R is emitted from the radiation source 36R to the breast pressed by the pressing plate 34, under the control of the console 12. Then, the radiation detector 30 generates a radiographic image on the basis of the radiation R transmitted through the breast. The image data of the captured radiographic image is transmitted to the console 12.

In a case where an ultrasound image is captured, the user applies an acoustic matching member (not illustrated), such as echo jelly, onto the upper surface 34A of the pressing plate 34. Further, the user operates the ultrasound probe 65 to scan the upper surface 34A of the pressing plate 34 covered by the acoustic matching member, with ultrasonic waves, thereby capturing an ultrasound image. The captured ultrasound image is displayed on the display unit 68 of the ultrasonography apparatus 16.

As an example, in the embodiment, in a case where the capture of a radiographic image by the mammography apparatus 10 and the capture of an ultrasound image are performed, when a series of imaging including the capture of an ultrasound image is entirely completed, the user instructs the pressing release, through the operation unit 26 of the mammography apparatus 10. Then, the deriving unit 86 determines whether or not the imaging by the mammography apparatus 10 is ended depending on whether or not the pressing release is instructed by the operation unit 26 of the mammography apparatus 10.

In step S116, the deriving unit 86 determines whether or not the pressing of the breast by the pressing plate 34 in the mammography apparatus 10 is released. In a case where the pressing of the breast is not released, the determination of step S116 is negative, and the process returns to step S102 to repeat the process of steps S102 to S114. For example, in a case where only the capture of a radiographic image is instructed in the imaging order but an ultrasound image is to be captured after the capture of a radiographic image, the user may input an imaging instruction of an ultrasound image through the operation unit 56 after the capture of a radiographic image, in some cases. In this case, the determination of step S102 after step S116 is affirmative, and the process of steps S102 to S114 is repeated.

On the other hand, in a case where the pressing of the breast is released, the determination of step S116 is affirmative, and the present control process is ended.

In the embodiment, in a case where the corrected limit depth is equal to or greater than the thickness of the breast, the imaging information 90 is not displayed. However, the present disclosure is not limited to the embodiment, and even in a case where the corrected limit depth is equal to or greater than the thickness of the breast, the imaging information 90 may be displayed on the display unit 58 under the control of the display control unit 89.

The embodiment may have following Modification Examples 1 to 3.

Modification Example 1

In the modification example, the display control unit 89 causes the display unit 58 to perform display by adding the imaging information 90 to a simulated image of the breast in the pressed state. FIG. 11A illustrates an example of the imaging information 90 displayed on the display unit 58 in the modification example. FIG. 11A illustrates a display example of a case of adding the imaging information 90 to a simulated image 92 including an image 92A indicating the imaging table 40, an image 92B in which the breast in the pressed state is simulated, and an image 92C in which the pressing plate 34 is simulated. The imaging information 90 illustrated in FIG. 11A includes a position information image 90A indicating the position of the limit depth, the imaging possible range, and the imaging impossible range, an information image 90B indicating that imaging is possible, and an information image 90C indicating that imaging is impossible.

In a case where the capture of a radiographic image of the breast in the pressed state has been already performed and the capture of a radiographic image is tomosynthesis imaging, when a plurality of reconstructed images obtained by reconstructing projection images generated by the tomosynthesis imaging are obtained, for example, the simulated image 92 illustrated in FIG. 11B may be displayed instead of the simulated image 92 illustrated in FIG. 11A. The reconstructed image is called a tomographic image, and is a radiographic image according to the height of the breast, specifically, the height of the breast from the imaging surface 40A of the imaging table 40. The imaging information 90 illustrated in FIG. 11B includes an interested-object image 92D, such as a mass or a calcification, which is displayed according to the position derived from the reconstructed image. The three-dimensional position of the interested object, and the position at least in the height direction may be derived from the reconstructed image by the deriving unit 86.

Modification Example 2

In the embodiment, an aspect in which the deriving unit 86 corrects the limit depth using the pressing member information has been described. However, information affecting the limit depth other than the pressing member information may be acquired and the limit depth (or the thickness of the breast) may be corrected according to the acquired information.

For example, the attenuation amount of ultrasonic waves differs depending on the amount of mammary glands of the breast, in other words, the mammary gland density of the breast. For example, as the amount of mammary glands of the breast is increased, in other words, as the mammary gland density of the breast is increased, the attenuation amount of ultrasonic waves is increased. As an example, in the modification example, a correction coefficient (not illustrated) used for correcting the limit depth according to the mammary gland density of the breast is stored in the storage unit 52 in advance. The mammary gland density is not limited to a specific value, classifications according to the mammary gland density, such as "fatty", "scattered mammary gland", "non-uniform high concentration", and "(extremely) high concentration" which are illustrated in the mammography guidelines may be used.

FIG. 12 illustrates a part of a flowchart illustrating an example of the flow of the control operation in the console 12 of the modification example. As illustrated in FIG. 12, the control process of the modification example is different from the control process (refer to FIG. 9) of the embodiment in that the process of step S111 is included instead of step S110.

In the modification example, the user inputs the mammary gland density through the operation unit 56. Thus, in step S111, the deriving unit 86 acquires mammary gland density information indicating the mammary gland density that is input by the user.

In a case where the capture of a radiographic image of the breast in the pressed state has already been performed, the deriving unit 86 may derive the mammary gland density from the radiographic image. For example, a known method, such as a technique that estimates a mammary gland content on the basis of a radiographic image and a fat image estimated from the radiographic image, described in JP2010-253245A, may be used as the method of deriving the amount of mammary glands from the radiographic image.

In step S112, the deriving unit 86 corrects the limit depth acquired in step S108 using the mammary gland density information acquired in step S111. As an example, the deriving unit 86 of the modification example acquires the correction coefficient according to the mammary gland density that the mammary gland density information indicates, from the storage unit 52 and corrects the limit depth using the acquired correction coefficient.

In the modification example, an aspect in which the limit depth is corrected using the mammary gland density information indicating the mammary gland density (amount of mammary glands) instead of the pressing member information has been described, but an aspect in which the limit depth is corrected using the mammary gland density information in addition to the pressing member information may be adopted.

The information affecting the limit depth other than the pressing member information is not limited to the mammary gland density (amount of mammary glands) described in the modification example. For example, since ultrasonic waves are attenuated by the acoustic matching member used in the capture of an ultrasound image, the limit depth may be corrected using information according to the acoustic matching member used in the capture of an ultrasound image as the information affecting the limit depth.

Modification Example 3

In the modification example, as in the example illustrated in FIG. 13, an aspect in which the medical imaging system 1 comprises a plurality of ultrasonography apparatuses 16 (in FIG. 13, four, ultrasonography apparatuses 16A to 16D) will be described. The ultrasonography apparatuses 16A to 16D correspond to the apparatus A to the apparatus D in the depth information 53 illustrated in FIG. 5, and the depth information 53 indicating the limit depth corresponding to each of the ultrasonography apparatuses 16A to 16D is stored in the storage unit 52 of the console 12.

FIG. 14 illustrates a part of a flowchart illustrating an example of the flow of the control operation in the console 12 of the modification example. As illustrated in FIG. 14, the control process of the modification example is different from the control process (refer to FIG. 9) of the embodiment in that the process of steps S106A, S108A, S112A, S114A, and S118A is included instead of steps S106, S108, S112, S114, and S118.

In step S106A, the depth information acquisition unit 84 acquires information indicating each of the ultrasonography apparatuses 16A to 16D. In step S108A, the depth information acquisition unit 84 acquires the limit depth corresponding to the acquired information indicating each of the ultrasonography apparatuses 16A to 16D, from the depth information 53 for each of the ultrasonography apparatuses 16A to 16D.

In step S112A, the deriving unit 86 corrects the limit depth acquired in step S108A using the pressing member information acquired in step S110 for each of the ultrasonography apparatuses 16A to 16D.

In step S114A, the deriving unit 86 determines whether or not there is an ultrasonography apparatus 16 in which the corrected limit depth is less than the thickness of the breast (the corrected limit depth<the thickness of the breast). In a case where there is no ultrasonography apparatus 16 in which the corrected limit depth is less than the thickness of the breast among the ultrasonography apparatuses 16A to 16D, in other words, in a case where the corrected limit depth is equal to or greater than the thickness of the breast for all of the ultrasonography apparatuses 16A to 16D, the determination of step S114A is negative, and the process proceeds to step S116. The ultrasonography apparatus 16 in which the corrected limit depth is equal to or greater than the thickness of the breast is an apparatus in which the capture of an ultrasound image of the breast in the current pressed state with predetermined accuracy or higher is possible.

On the other hand, in a case where there is an ultrasonography apparatus 16 in which the corrected limit depth is less than the thickness of the breast among the ultrasonography apparatuses 16A to 16D, the determination of step S114A is affirmative, and the process proceeds to step S118A. The ultrasonography apparatus 16 in which the corrected limit depth is less than the thickness of the breast is an apparatus which cannot capture an ultrasound image of the breast in the current pressed state with predetermined accuracy or higher, in other words, which has low accuracy of the ultrasound image.

In step S118A, the display control unit 89 performs control of causing the display unit 58 to display, as the imaging information 90, the information relating to all of the ultrasonography apparatuses 16 having low accuracy of the ultrasound image on the basis of the imaging information, and the present control process is ended. The information that the display control unit 89 causes the display unit 58 to display as the imaging information 90 may be, for example, information indicating all of the ultrasonography apparatuses 16 having low accuracy of the ultrasound image, and specifically, may be the name of the ultrasonography apparatus 16. For example, an aspect in which the imaging information 90 according to the ultrasonography apparatus 16 illustrated in FIG. 10 is displayed for all of the ultrasonography apparatuses 16 having low accuracy of the captured ultrasound image may be adopted.

The display of the imaging information 90 is not limited to the modification example. For example, contrary to the modification example, the display control unit 89 may perform control of causing the display unit 58 to display, as the imaging information 90, the information relating to all of the ultrasonography apparatuses 16 satisfying the accuracy of the ultrasound image.

Figure 15A:
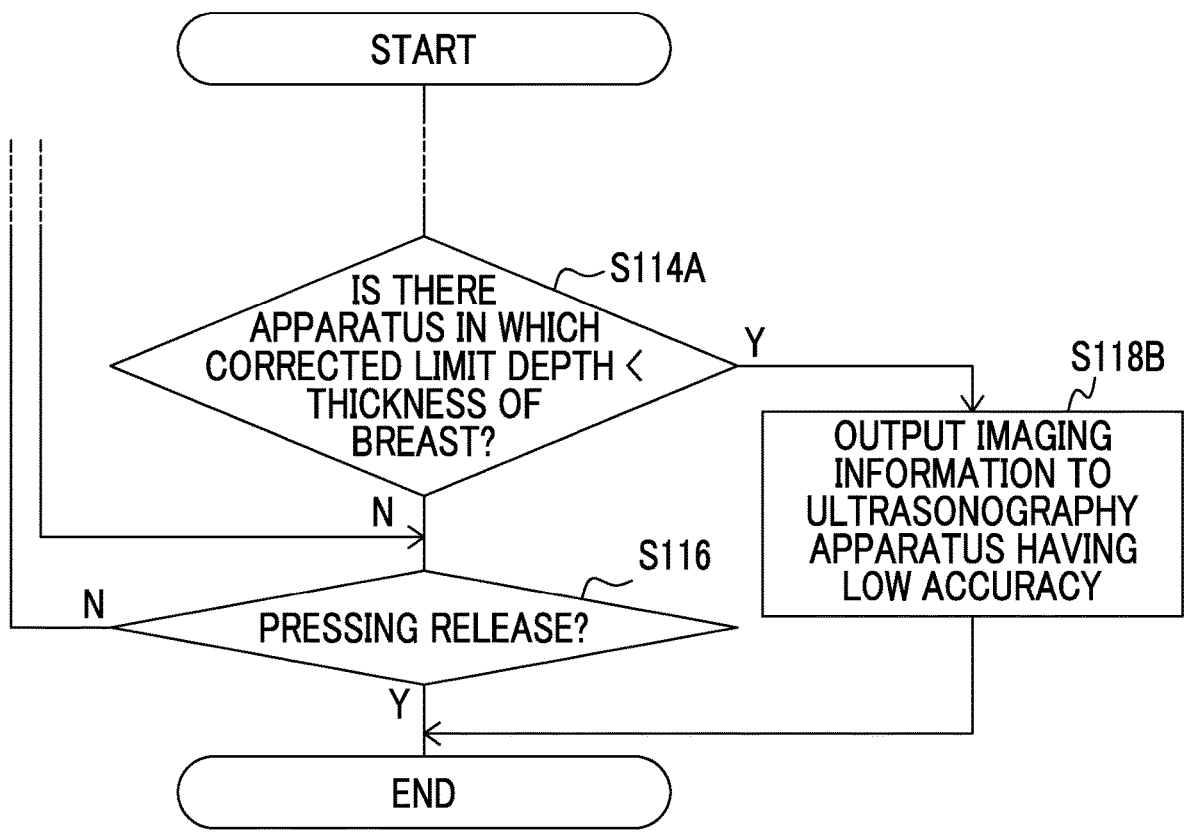
FIG. 15A is a flowchart illustrating another example of a part of the flow of the control process in the console of Modification Example 3.

For example, a part of the control process illustrated in FIG. 15A may be adopted. In the control process illustrated in FIG. 15A, the process of step S118B is executed instead of step S118A in the control process (refer to FIG. 14) of the modification example. In step S118B of FIG. 15A, the output unit 88 outputs the imaging information 90 to all of the ultrasonography apparatuses 16 having low accuracy of the ultrasound image, and the present control process is ended. It is preferable that the output unit 88 outputs the imaging information 90, which is illustrated in FIG. 10, according to each ultrasonography apparatus 16, to each ultrasonography apparatus 16. In the ultrasonography apparatus 16 which has received the imaging information 90 in response to the process of step S118B, the control unit 60 performs control of causing the display unit 68 to display the imaging information 90.

Figure 15B:
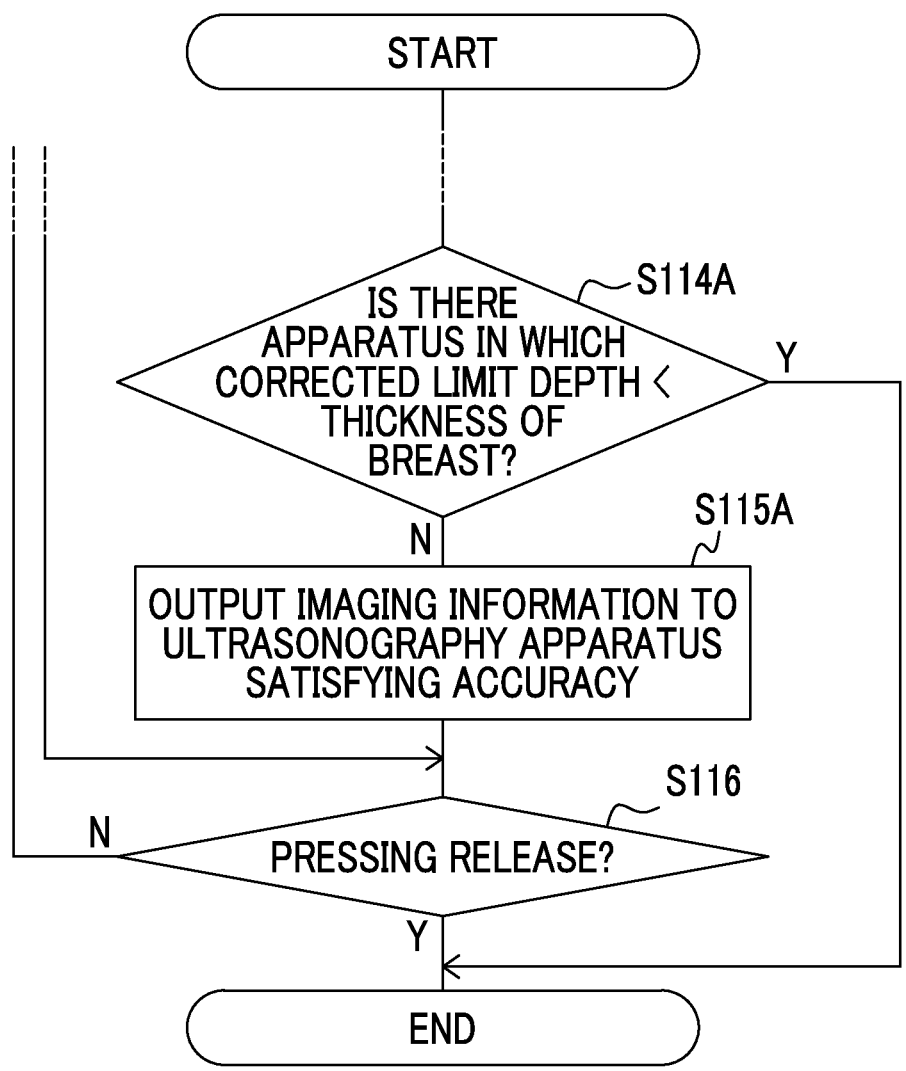
FIG. 15B is a flowchart illustrating another example of a part of the flow of the control process in the console of Modification Example 3.

For example, a part of the control process illustrated in FIG. 15B may be adopted. In the control process illustrated in FIG. 15B, the process of step S115A is executed between step S114A and step S116 in the control process (refer to FIG. 14) of the modification example and the process of step S118A is not executed. In step S115A of FIG. 15B, the output unit 88 outputs the imaging information 90 to all of the ultrasonography apparatuses 16 satisfying the accuracy of the ultrasound image. It is preferable that the output unit 88 outputs the imaging information 90, which is illustrated in FIG. 10, according to each ultrasonography apparatus 16, to each ultrasonography apparatus 16. In the ultrasonography apparatus 16 which has received the imaging information 90 in response to the process of step S115A, the control unit 60 performs control of causing the display unit 68 to display the imaging information 90.

Second Embodiment

Hereinafter, a second embodiment will be described in detail.

In the embodiment, an aspect in which in a case where both a radiographic image and an ultrasound image are captured while the breast is in pressed state by the pressing plate 34, a radiographic image is captured first, in other words, a radiographic image is not captured after an ultrasound image is captured will be described.

Since the overall configuration (refer to FIG. 1) of the medical imaging system 1 of the embodiment is the same as that in the first embodiment, the description thereof will not be repeated. In the embodiment, since the functional configuration of the console 12 is partially different from that of the console 12 of the first embodiment, the different configuration will be described.

Figure 16:
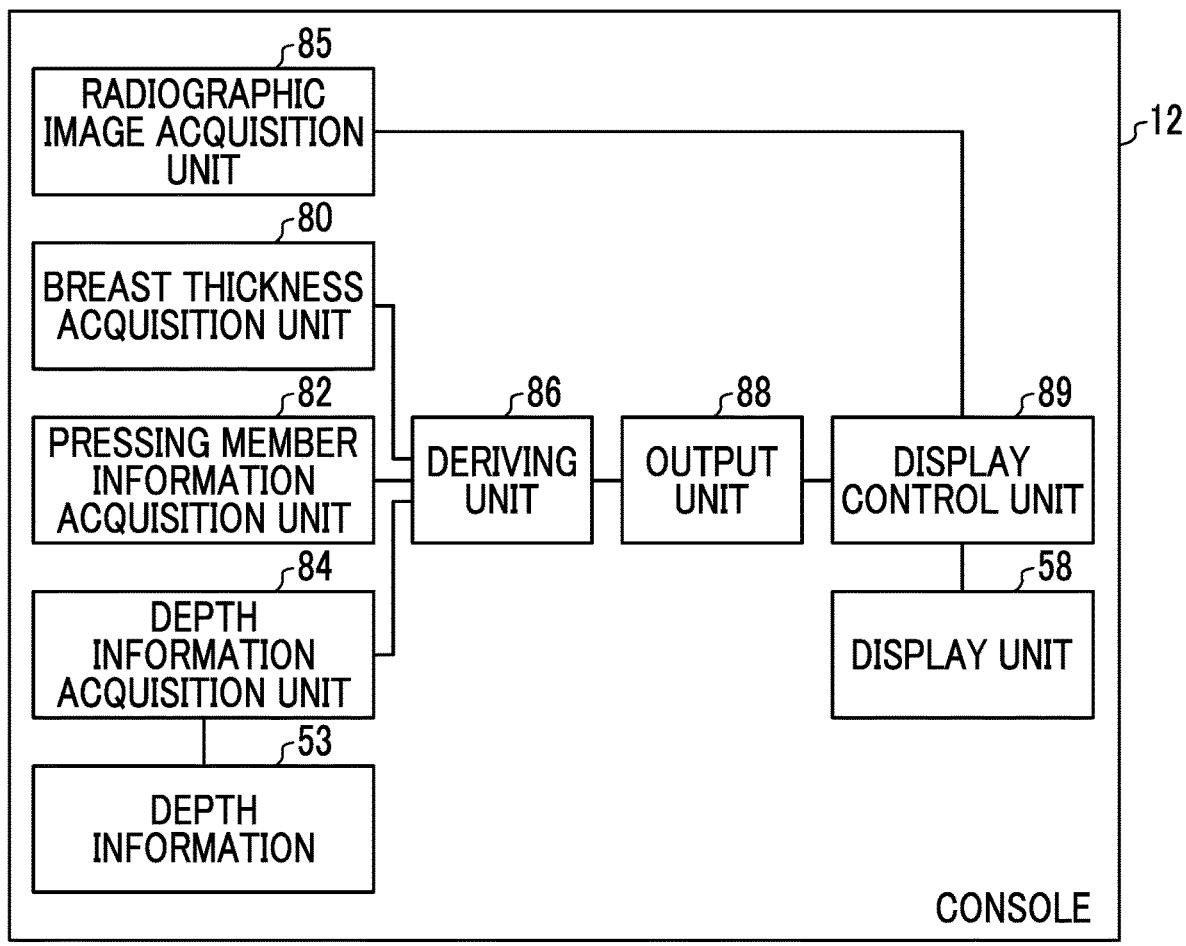
FIG. 16 is a functional block diagram illustrating an example of the function of a console of a second embodiment.

FIG. 16 is a functional block diagram illustrating an example of the configuration of the console 12 of the embodiment. As illustrated in FIG. 16, the console 12 of the embodiment is different from the console 12 (refer to FIG. 6) of the first embodiment in that a radiographic image acquisition unit 85 is further included.

The radiographic image acquisition unit 85 acquires a plurality of reconstructed images according to the height of the breast, which are obtained by reconstructing a plurality of projection images generated by tomosynthesis imaging by the mammography apparatus 10. The method for the radiographic image acquisition unit 85 to acquire a plurality of reconstructed images is not particularly limited. In a case where the mammography apparatus 10 generates a plurality of reconstructed images from the projection image, the radiographic image acquisition unit 85 may acquire the reconstructed images from the mammography apparatus 10. In addition, for example, an aspect in which the radiographic image acquisition unit 85 generates a plurality of reconstructed images by acquiring a plurality of projection images obtained by tomosynthesis imaging from the mammography apparatus 10 and generating a plurality of reconstructed images from the acquired projection images may be adopted. The method of generating a plurality of reconstructed images is not particularly limited, and for example, a plurality of reconstructed images may be generated from a plurality of projection images using a known back projection method such as a simple back projection method or a filtered back projection method.

The plurality of reconstructed images acquired by the radiographic image acquisition unit 85 are output to the display control unit 89.

The display control unit 89 of the embodiment performs control of causing the display unit 58 to display the reconstructed images, the information indicating the height of the reconstructed image, and the imaging information 90 associated with the information indicating the height.

Figure 17:
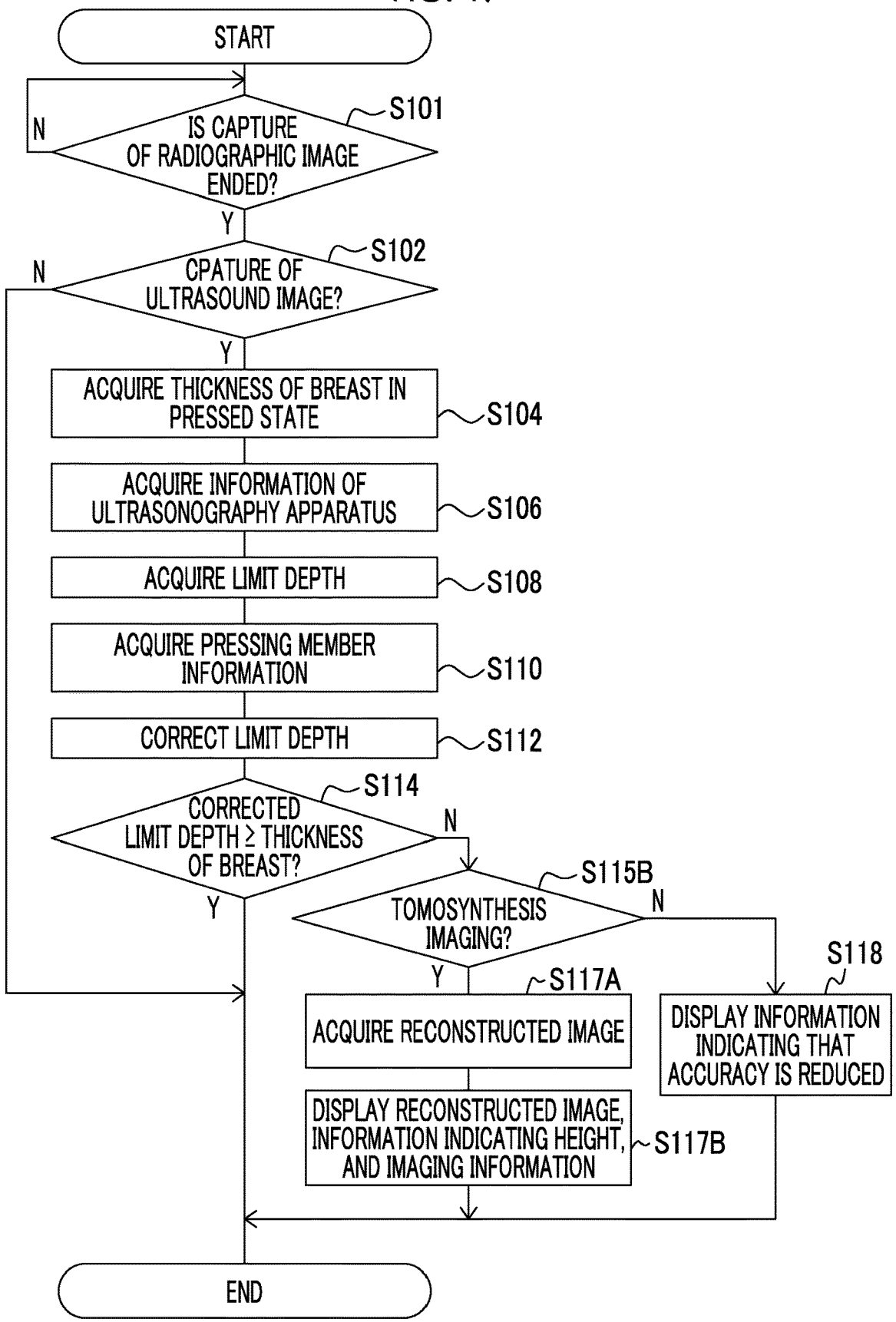
FIG. 17 is a flowchart illustrating an example of the flow of a control process in the console of the second embodiment.

FIG. 17 is a flowchart illustrating an example of the flow of the control operation in the console 12 of the embodiment. As illustrated in FIG. 17, the control process of the embodiment is different from the control process (refer to FIG. 9) of the first embodiment in that the process of step S101 is included instead of step S100, the process of step S115B, step S117A, and step S117B is performed after step S114, and the process of step S116 is not included.

As illustrated in FIG. 17, in a case where the present control process is started, in step S101, the deriving unit 86 determines whether or not the capture of a radiographic image by the mammography apparatus 10 is ended. As described above, in a case where a radiographic image is captured, the radiation detector 30 generates a radiographic image and outputs image data indicating the generated radiographic image to the console 12. Until the console 12 receives the image data indicating the radiographic image from the mammography apparatus 10, the determination of step S101 is negative. On the other hand, in a case where the console 12 receives the image data indicating the radiographic image from the mammography apparatus 10, the determination of step S101 is affirmative, and the process proceeds to step S102.

In addition, in a case where the determination of step S114 is negative, in other words, in a case where the corrected limit depth is less than the thickness of the breast, the radiographic image acquisition unit 85 determines whether or not the capture of a radiographic image by the mammography apparatus 10 is tomosynthesis imaging in step S115B. As an example, in a case where tomosynthesis imaging is instructed in the imaging order, the radiographic image acquisition unit 85 of the embodiment determines that the capture of a radiographic image by the mammography apparatus 10 is tomosynthesis imaging. In a case where the capture of a radiographic image by the mammography apparatus 10 is not tomosynthesis imaging, the determination of step S115B is negative, and the process proceeds to step S118. On the other hand, in a case where the capture of a radiographic image by the mammography apparatus 10 is tomosynthesis imaging, the determination of step S115B is affirmative, and the process proceeds to step S117A.

In step S117A, the radiographic image acquisition unit 85 acquires the reconstructed image as described above. In step S117B, the display control unit 89 performs control of causing the display unit 58 to display the reconstructed images, the information indicating the height of the reconstructed image, and the imaging information 90, and the present control process is ended.

Figure 18A:
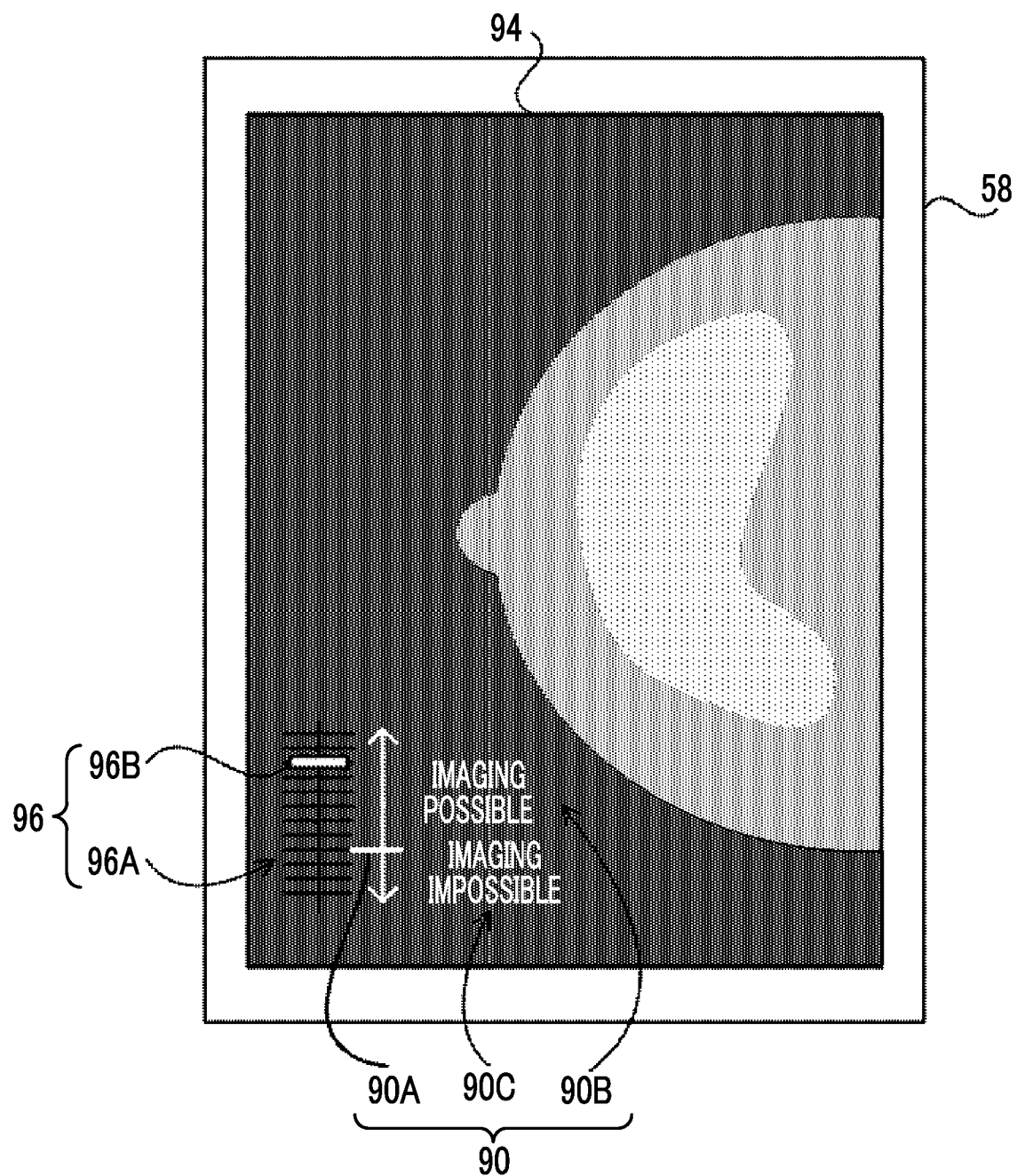
FIG. 18A is a diagram illustrating an example of a reconstructed image, information indicating the height, and imaging information which are displayed on a display unit in a third embodiment.

FIG. 18A illustrates an example of the reconstructed image, the information indicating the height of the reconstructed image, and the imaging information 90 which are displayed on the display unit 58 under the control of the display control unit 89. In the example illustrated in FIGS. 18A and 18B, an aspect in which a reconstructed image 94, an image 96 of the information indicating the height, and the imaging information 90 are displayed is illustrated. The image 96 includes an image 96A of a memory indicating the height, and an image 96B indicating the height (position) of the reconstructed image 94 which is currently displayed on the display unit 58. In the embodiment, the user operates the operation unit 56 to change the position of the image 96B along the image 96A, so that the reconstructed image 94 having a height according to the changed position is displayed on the display unit 58.

Similar to the imaging information 90 illustrated in FIGS. 11A and 11B, the imaging information 90 illustrated in FIG. 18A includes the position information image 90A indicating the imaging possible range and the imaging impossible range, the information image 90B indicating that imaging is possible, and the information image 90C indicating that imaging is impossible.

Figure 18B:
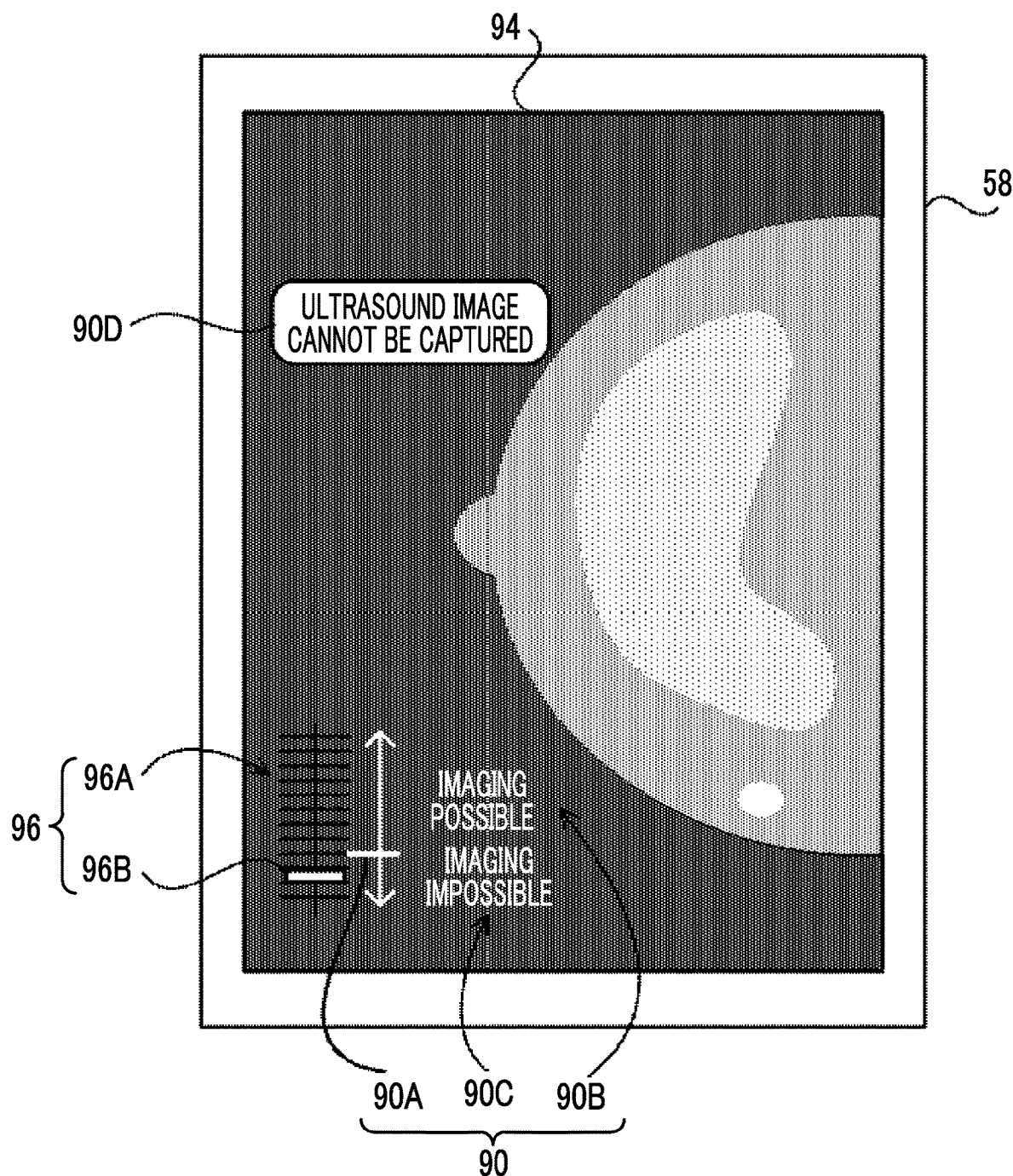
FIG. 18B is a diagram illustrating another example of the reconstructed image, the information indicating the height, and the imaging information which are displayed on the display unit in the third embodiment.

The reconstructed image, the information indicating the height of the reconstructed image, and the imaging information 90 which are displayed on the display unit 58 are not limited to the example illustrated in FIG. 18A. For example, as illustrated in FIG. 18B, the imaging information 90 may further include an information image 90D indicating whether or not the capture of an ultrasound image is possible. In the example illustrated in FIG. 18B, the reconstructed image 94 within a range where the capture of an ultrasound image is impossible is displayed on the display unit 58, and the image of the information indicating that the capture of an ultrasound image is impossible is displayed as the information image 90D. In a case where the reconstructed image 94 within a range where the capture of an ultrasound image is possible is displayed on the display unit 58, the information image 90D may not be displayed on the display unit 58.

In this way, the reconstructed image, the information indicating the height of the reconstructed image, and the imaging information 90 are displayed so that the user knows which reconstructed image 94 the ultrasound image corresponding to cannot be obtained. For example, in a case where the reconstructed image 94 including an image of the interested object is an image within a range where the capture of an ultrasound image is impossible, even when the ultrasound image is captured by the ultrasonography apparatus 16 while the breast is in the pressed state by the pressing plate 34, the user knows that there is a high possibility that the interested object is not imaged.

Third Embodiment

Hereinafter, a third embodiment will be described in detail.

Since the overall configuration (refer to FIG. 1) of the medical imaging system 1 of the embodiment is the same as that in the first embodiment, the description thereof will not be repeated. In the embodiment, since the information stored in the storage unit 52 of the console 12 and the functional configuration of the console 12 are partially different from those of the console 12 of the first embodiment, the different configuration will be described.

Figure 19:
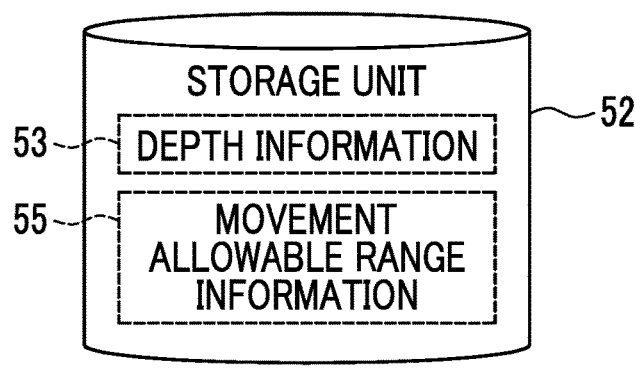
FIG. 19 is a diagram illustrating an example of information stored in a storage unit of a console of the third embodiment.

As illustrated in FIG. 19, the storage unit 52 of the console 12 of the embodiment is different from the console 12 (refer to FIG. 2) of the first embodiment in that movement allowable range information 55 is further stored. The movement allowable range information 55 is information indicating an allowable range of the movement in the height direction of the pressing plate 34, specifically, in the pressing direction. The pressing plate 34 may be moved in the pressing direction after a certain amount of time has passed since the breast is in the pressed state by the pressing plate 34, in some cases. Thus, in the embodiment, the movement allowable range information 55 indicating an allowable range in which the movement of the pressing plate 34 in the pressing direction is allowed is stored in the storage unit 52.

Figure 20:
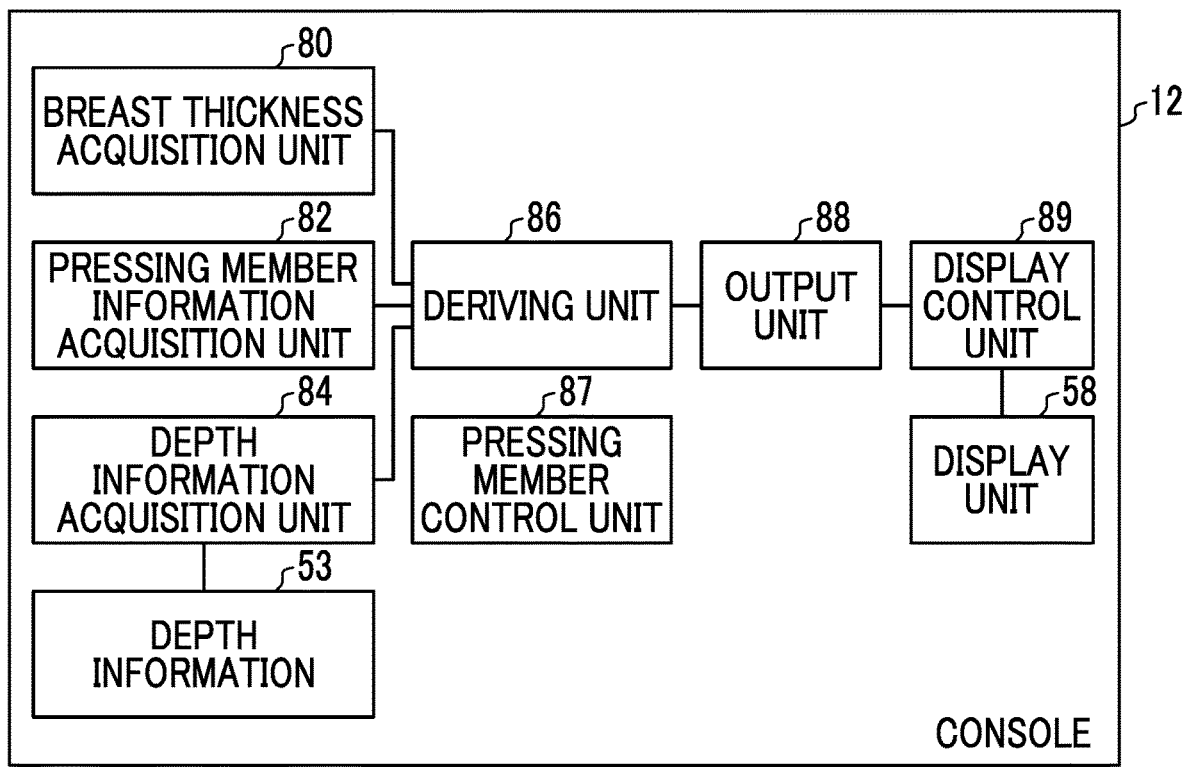
FIG. 20 is a functional block diagram illustrating an example of the function of the console of the third embodiment.

FIG. 20 is a functional block diagram illustrating an example of the configuration of the console 12 of the embodiment. As illustrated in FIG. 20, the console 12 of the embodiment is different from the console 12 (refer to FIG. 6) of the first embodiment in that a pressing member control unit 87 is further included. In a case where the difference between the thickness of the breast and the corrected limit depth is within a movement allowable range, the pressing member control unit 87 outputs an instruction to move the pressing plate 34 to a position corresponding to the limit depth, specifically, a position where the height of the pressing plate 34 from the imaging surface 40A of the imaging table 40 is the same height as the limit depth, to the mammography apparatus 10.

Figure 21:
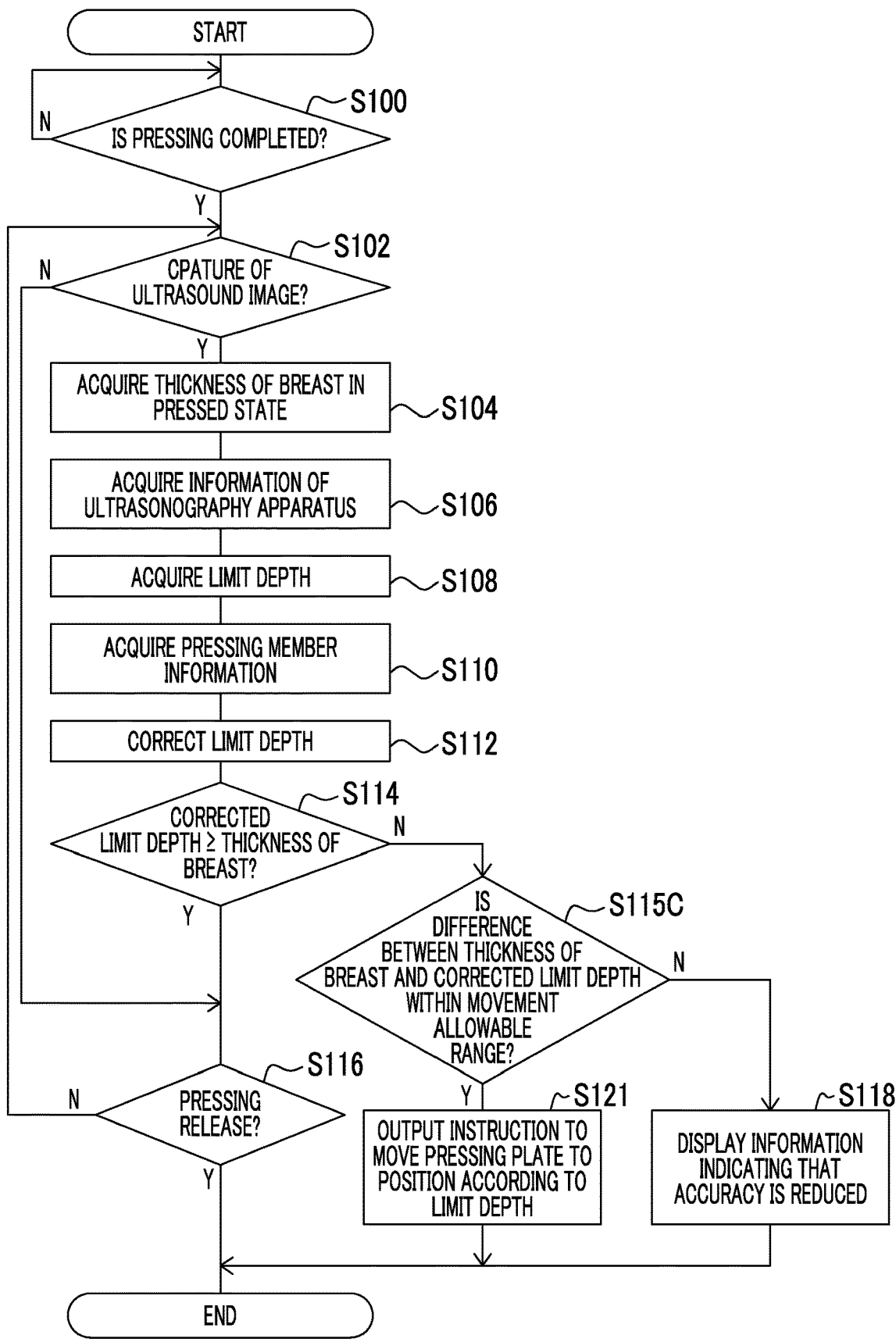
FIG. 21 is a flowchart illustrating another example of a part of the flow of the control process in the console of the third embodiment.

FIG. 21 is a flowchart illustrating an example of the flow of the control operation in the console 12 of the embodiment. As illustrated in FIG. 21, the control process of the embodiment is different from the control process (refer to FIG. 9) of the first embodiment in that the process of steps S115C and S121 is included.

As illustrated in FIG. 21, in a case where the determination of step S114 is negative, in other words, in a case where the corrected limit depth is less than the thickness of the breast, the pressing member control unit 87 determines whether or not the difference between the thickness of the breast and the corrected limit depth is within the movement allowable range in step S115C. Specifically, the pressing member control unit 87 acquires the movement allowable range information 55 from the storage unit 52. In addition, the pressing member control unit 87 derives the difference between the thickness of the breast and the corrected limit depth, and determines whether or not the derived difference is included in the movement allowable range acquired from the movement allowable range information 55. In a case where the difference between the thickness of the breast and the corrected limit depth is not within the movement allowable range, the determination of step S115C is negative, and the process proceeds to step S118.

On the other hand, in a case where the difference between the thickness of the breast and the corrected limit depth is within the movement allowable range, the determination of step S115C is affirmative, and the process proceeds to step S121. In step S121, the pressing member control unit 87 outputs an instruction to move the pressing plate 34 to a position corresponding to the limit depth, to the mammography apparatus 10, and the present control process is ended. In the mammography apparatus 10, the pressing plate driving unit 32 drives the pressing plate 34 to causes the position of the pressing plate 34 to be the position of the height corresponding to the limit depth, according to the instruction output from the console 12.

In this way, in the embodiment, in a case where the difference between the thickness of the breast and the corrected limit depth is within the movement allowable range, it is possible to set the thickness of the breast in the pressed state by the pressing plate 34 to be equal to or less than the limit depth by moving the pressing plate 34. Accordingly, it is possible to improve the frequency at which the capture of an ultrasound image is possible, and it is possible to improve the accuracy of the ultrasound image.

In a case where the pressing plate 34 can be moved in the pressing direction, the movement allowable range in which the movement of the pressing plate 34 is allowed may be determined depending on the pressing pressure at which the pressing plate 34 presses the breast, the current thickness of the breast in the pressed state, the stiffness of the breast, the mammary gland density, and the like, in some cases. In this case, it is preferable that the movement allowable range associated with those kinds of information is stored in the storage unit 52 as the movement allowable range information 55. Further, it is preferable that the pressing member control unit 87 acquires at least one of those kinds of information, and acquires the movement allowable range according to the acquired information from the movement allowable range information 55.

As described above, the console 12 of each of the above-described embodiments comprises the breast thickness acquisition unit 80, the depth information acquisition unit 84, the deriving unit 86, and the output unit 88. The breast thickness acquisition unit 80 acquires the thickness of the breast which is in the pressed state by the pressing plate 34. In a case where an ultrasound image of the breast in the pressed state is captured, the depth information acquisition unit 84 acquires the limit depth from the depth information 53 indicating the depth to which imaging by the ultrasonography apparatus 16 which captures the ultrasound image is possible. The deriving unit 86 derives the imaging information 90 indicating whether or not it is possible for the ultrasonography apparatus 16 to capture an ultrasound image with predetermined accuracy or higher, on the basis of the thickness of the breast acquired by the breast thickness acquisition unit 80 and the limit depth acquired by the depth information acquisition unit 84. The output unit 88 outputs the imaging information 90 derived by the deriving unit 86.

In a case where the thickness of the breast is greater than the limit depth of the ultrasonography apparatus 16, the capture of the ultrasound image by the ultrasonography apparatus 16 has the predetermined accuracy or lower, and thus imaging becomes impossible in some cases. In contrast to this, with the console 12 of each of the above-described embodiments, in a case where the thickness of the breast is greater than the limit depth of the ultrasonography apparatus 16, the imaging information 90 indicating that the capture of an ultrasound image with the predetermined accuracy or higher is not possible can be output.

In this manner, even in a case where an ultrasound image is captured by the ultrasonography apparatus 16 while maintaining the current pressed state, the user knows that an ultrasound image having accuracy less than the predetermined accuracy is captured. For example, in a case where an ultrasound image is captured while maintaining the current pressed state so that an ultrasound image having accuracy less than the predetermined accuracy is obtained, it is possible for the user to check that the reduction in accuracy is due to the performance of the ultrasonography apparatus 16 (ultrasound probe 65) rather than the setting of the ultrasonography apparatus 16 (ultrasound probe 65). Even in a case where the thickness of the breast exceeds the corrected limit depth, in some cases, the ultrasound image may be captured while maintaining the current pressed state for the reference or a case where the height of the site of interest is within the imaging possible range. In such a case, it is preferable that the console 12 outputs, to the ultrasonography apparatus 16, an instruction to add the information indicating that the accuracy of the ultrasound image is equal to or less than the predetermined accuracy or that the height of the interested object is within the imaging possible range, to the ultrasound image.

According to the above-described embodiments, since it is possible to suppress that the ultrasound image having accuracy less than the predetermined accuracy is captured, it is possible to reduce the burden on the subject due to re-imaging or the like.

In a case where an ultrasound image is captured by the ultrasonography apparatus 16 while maintaining the current pressed state so that an ultrasound image having accuracy less than the predetermined accuracy is captured, for example, the pressing of the breast is released and imaging according to a normal imaging method for an ultrasound image (imaging without the pressing by the pressing plate 34) may be performed.

The present disclosure is not limited to the above-described embodiments, and since the pressing member information is changed when the pressing plate 34 is changed, an aspect in which in a case where there is a possibility that the thickness of the breast in the pressed state by the pressing plate 34 is less than the limit depth, the display control unit 89 performs control of causing the display unit 58 to display the content suggesting the change of the pressing plate 34 may be adopted.

In the above-described embodiments, an aspect in which the imaging information 90 is visibly displayed on the display unit 58 has been described, but in a case where the display unit 58 includes a speaker or the like, the imaging information 90 may be audibly displayed using voice.

As aspect in which by the user designating, through the operation unit 56, an interested object in a normal (two-dimensional) radiographic image or the reconstructed image 94 displayed on the display unit 58 under the control of the display control unit 89 in a case where the radiographic image acquisition unit 85 acquires the reconstructed image as in the third embodiment, whether or not the image including the designated interested object has the predetermined accuracy or higher is determined and the determination result is displayed may be adopted. Specifically, an aspect in which whether or not the height of the designated interested object is within the imaging possible range is determined may be adopted.

Figure 22:
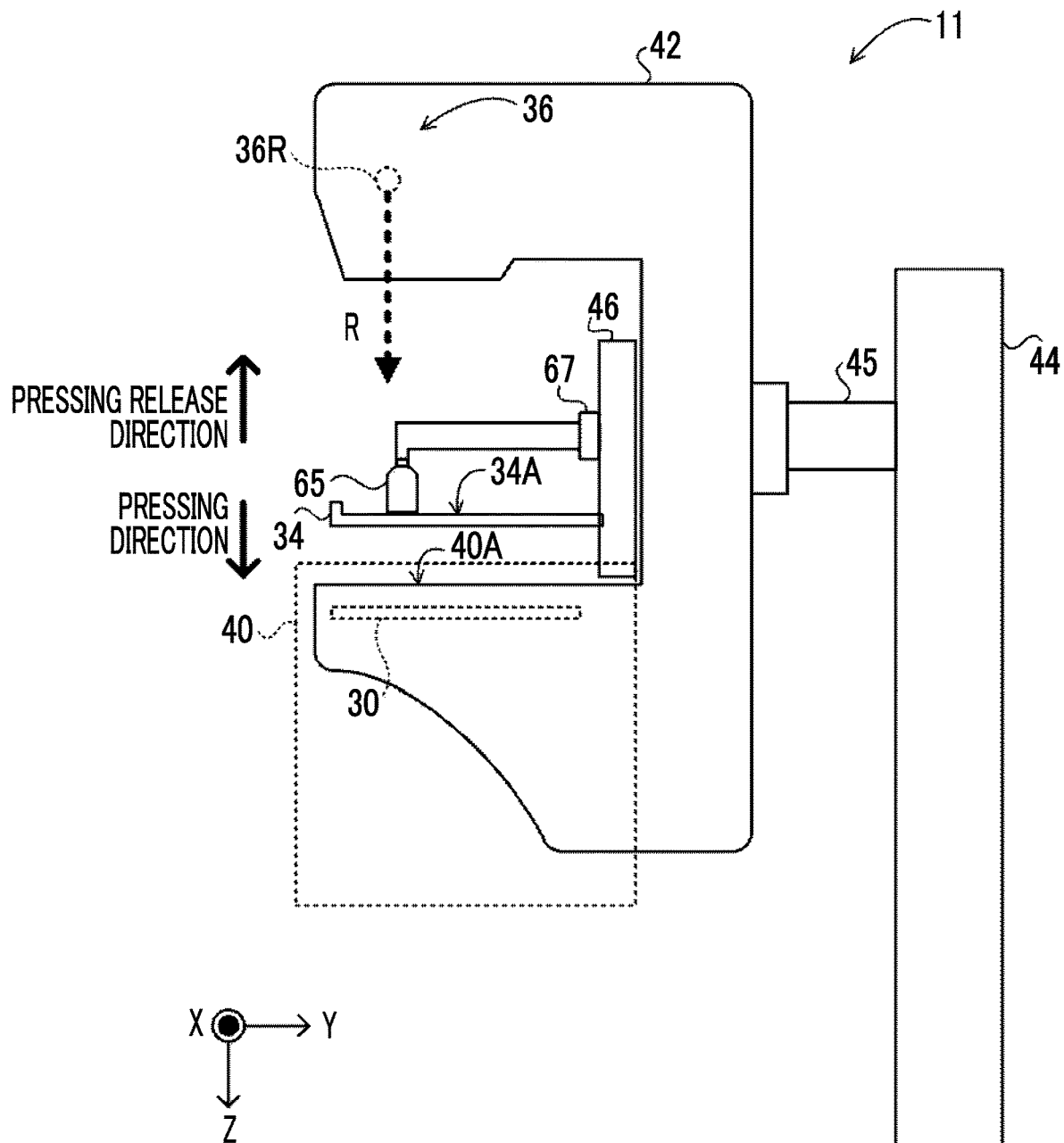
FIG. 22 is a side view illustrating an example of the appearance of a medical imaging apparatus of an embodiment.

In the above-described embodiments, an aspect in which the mammography apparatus 10 and the ultrasonography apparatus 16 are separated has been described, but as illustrated in FIG. 22, the mammography apparatus 10 and the ultrasonography apparatus 16 may be integrated to form a medical imaging apparatus 11. In the medical imaging apparatus 11 illustrated in FIG. 22, the ultrasound probe 65 is moved along the upper surface (a surface opposite to the surface that comes into contact with the breast of the subject) 34A of the pressing plate 34 by a probe moving mechanism 67 and scans the breast with ultrasonic waves to automatically acquire an ultrasound image of the breast, so that an ultrasound image is automatically captured.

In the above-described embodiments, an aspect in which the mammography apparatus 10 or the console 12 functions as the control device of the present disclosure has been described, but the apparatus functioning as the control device of the present disclosure is not limited to the console 12. For example, the mammography apparatus 10 or the like may function as the control device of the present disclosure, or the function of the control device of the present disclosure may be realized by a plurality of apparatuses such as the mammography apparatus 10 and the console 12.

In the above-described embodiments, for example, the following various processors can be used as the hardware structure of processing units executing various processes such as the breast thickness acquisition unit 80, the pressing member information acquisition unit 82, the depth information acquisition unit 84, the deriving unit 86, the output unit 88, and the display control unit 89. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (program) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software as typified by a computer such as a client or a server, and this processor functions as a plurality of processing units. A second example of the configuration is an aspect in which a processor fulfilling the functions of the entire system including a plurality of processing units by one integrated circuit (IC) chip as typified by a system on chip (SoC) or the like is used. As such, various processing units are configured by using one or more of the various processors as a hardware structure.

In addition, specifically, an electric circuit (circuitry) obtained by combining circuit elements, such as semiconductor elements, can be used as the hardware structure of the various processors.

In the above-described embodiments, an aspect in which the control processing program 51 is stored (installed) in the ROM 50B in advance has been described. However, the present disclosure is not limited thereto. The control processing program 51 may be provided by being recorded in a recording medium, such as a compact disc read only memory (CD-ROM), a digital versatile disc read only memory (DVD-ROM), or a universal serial bus (USB) memory. In addition, the control processing program 51 may be downloaded from an external device through a network.

For example, the configurations and operations of the medical imaging system 1, the radiography system 2, the mammography apparatus 10, the ultrasonography apparatus 16, and the like described in the above-described embodiments are illustrative and may be changed according to the situation, without departing from the scope of the invention. It goes without saying that the above-described embodiments can be combined appropriately.

What is claimed is:

1. A control device comprising:
a memory; and
a processor coupled to the memory, the processor configured to:
acquire a thickness of a breast in a pressed state by a pressing member;
in a case where an ultrasound image of the breast in the pressed state is captured, acquire depth information indicating a depth to which imaging by at least one ultrasonography apparatus which captures the ultrasound image is possible;
derive imaging information indicating whether or not capture of an ultrasound image having predetermined accuracy or higher is possible by the at least one ultrasonography apparatus on the basis of the thickness of the breast and the depth information; and
output the imaging information;
wherein the processor is further configured to acquire pressing member information indicating at least one of a thickness of the pressing member or hardness of the pressing member,
and wherein the processor is further configured to derive the imaging information on the basis of the thickness of the breast, the depth information, and the pressing member information.

2. The control device according to claim 1, wherein the processor is configured to derive the imaging information indicating that the capture of the ultrasound image does not satisfy the predetermined accuracy in a case where the thickness of the breast is thicker than a thickness corresponding to the depth indicated by the depth information.

3. The control device according to claim 1, wherein the processor is configured to derive the imaging information indicating that the capture of the ultrasound image satisfies the predetermined accuracy in a case where the thickness of the breast is equal to or less than a thickness corresponding to the depth indicated by the depth information.

4. The control device according to claim 1, wherein:
the control device is connected to a plurality of the ultrasonography apparatuses,
the processor is configured to acquire the depth information of each of the plurality of the ultrasonography apparatuses, and
the processor is configured to derive the depth information for each of the plurality of ultrasonography apparatuses.

5. The control device according to claim 4, wherein the processor is configured to output the imaging information only to any ultrasonography apparatus for which the imaging information indicating that the capture of the ultrasound image satisfies the derived predetermined accuracy, among the plurality of ultrasonography apparatuses.

6. The control device according to claim 4, wherein the processor is configured to output the imaging information only to any ultrasonography apparatus for which the imaging information indicating that the capture of the ultrasound image does not satisfy the derived predetermined accuracy, among the plurality of ultrasonography apparatuses.

7. The control device according to claim 1, wherein in a case where capture of a radiographic image of the breast by a radiography apparatus and the capture of the ultrasound image of the breast are continuously performed while the breast is in the pressed state,
the processor is configured to:
derive the imaging information before the capture of the radiographic image, and
output the imaging information before the capture of the radiographic image.

8. The control device according to claim 1, wherein, in a case where capture of a radiographic image of the breast by a radiography apparatus and the capture of the ultrasound image of the breast are continuously performed while the breast is in the pressed state,
the processor is configured to:
derive the imaging information before the capture of the ultrasound image and after the capture of the radiographic image, and
output the imaging information before the capture of the ultrasound image and after the capture of the radiographic image.

9. The control device according to claim 8, wherein the processor is further configured to:
acquire a plurality of reconstructed images obtained by reconstructing radiographic images captured at different irradiation angles, which are obtained, in a case where the capture of the radiographic image is tomosynthesis imaging in which a radiation source irradiates the breast with radiation at the irradiation angles and a radiation detector captures the radiographic image at each of the irradiation angles; and
control a display unit to display the reconstructed image, information indicating a position of the breast in a height direction indicated by the reconstructed image, and the imaging information associated with the information indicating the position in the height direction.

10. The control device according to claim 9, wherein the processor is configured to control the display unit to display the imaging information in association with the reconstructed image in a case where the display unit displays the reconstructed image within a range where the capture of the ultrasound image does not satisfy the predetermined accuracy on the basis of the imaging information.

11. The control device according to claim 1, wherein the processor if further configured to control a display unit to display the imaging information output by the output unit.

12. The control device according to claim 1, wherein the processor is further configured to control a display unit to display an image simulating the breast in the pressed state by adding information indicating at least one of a region where the predetermined accuracy is satisfied or a region where the predetermined accuracy is not satisfied to the image.

13. The control device according to claim 1, wherein the processor is configured to derive the imaging information on the basis of the thickness of the breast, the depth information, and mammary gland density of the breast.

14. The control device according to claim 1, wherein the processor is further configured to, in a case where a difference between the thickness of the breast and a thickness corresponding to the depth indicated by the depth information is within a movement allowable range of the pressing member, which presses the breast, in a height direction, on the basis of information indicating the movement allowable range, control to move the pressing member to a position where the thickness of the breast in the pressed state becomes the depth indicated by the depth information.

15. A medical imaging system comprising:
a mammography apparatus which includes a radiation source, a radiation detector, and a pressing member that presses a breast disposed between the radiation source and the radiation detector to a pressed state, and which causes the radiation detector to capture a radiographic image of the breast in the pressed state;
an ultrasonography apparatus that captures an ultrasound image of the breast in the pressed state by the pressing member of the mammography apparatus; and
the control device according to claim 1, which controls capture of the ultrasound image by the ultrasonography apparatus.

16. A medical imaging system comprising:
a medical imaging apparatus which includes a radiation source, a radiation detector, and a pressing member that presses a breast disposed between the radiation source and the radiation detector to a pressed state, which causes the radiation detector to capture a radiographic image of the breast in the pressed state, and which captures an ultrasound image of the breast in the pressed state; and
the control device according to claim 1, which controls the medical imaging apparatus.

17. A control method for a computer to execute a process comprising:
acquiring a thickness of a breast in a pressed state by a pressing member;
in a case where an ultrasound image of the breast in the pressed state is captured, acquiring depth information indicating a depth to which imaging by an ultrasonography apparatus which captures the ultrasound image is possible;
deriving imaging information indicating whether or not capture of an ultrasound image having predetermined accuracy or higher is possible by the ultrasonography apparatus on the basis of the acquired thickness of the breast and the acquired depth information;
outputting the derived imaging information;
acquiring pressing member information indicating at least one of a thickness of the pressing member or hardness of the pressing member, and
deriving the imaging information on the basis of the thickness of the breast, the depth information, and the pressing member information.

18. A non-transitory computer readable medium storing a control program causing a computer to execute a process comprising:
acquiring a thickness of a breast in a pressed state by a pressing member;
in a case where an ultrasound image of the breast in the pressed state is captured, acquiring depth information indicating a depth to which imaging by an ultrasonography apparatus which captures the ultrasound image is possible;
deriving imaging information indicating whether or not capture of an ultrasound image having predetermined accuracy or higher is possible by the ultrasonography apparatus on the basis of the acquired thickness of the breast and the acquired depth information;
outputting the derived imaging information;

acquiring pressing member information indicating at least one of a thickness of the pressing member or hardness of the pressing member, and
deriving the imaging information on the basis of the thickness of the breast, the depth information, and the pressing member information.

19. A control device comprising:
a memory; and
a processor coupled to the memory, the processor configured to:
acquire a thickness of a breast in a pressed state by a pressing member;
in a case where an ultrasound image of the breast in the pressed state is captured, acquire depth information indicating a depth to which imaging by an ultrasonography apparatus which captures the ultrasound image is possible;
derive imaging information indicating whether or not capture of an ultrasound image having predetermined accuracy or higher is possible by the ultrasonography apparatus on the basis of the thickness of the breast and the depth information; and
output the imaging information;
wherein the processor is configured to derive the imaging information indicating that the capture of the ultrasound image satisfies the predetermined accuracy in a case where the thickness of the breast is equal to or less than a thickness corresponding to the depth indicated by the depth information.

20. A control device comprising:
a memory; and
a processor coupled to the memory, the processor configured to:
acquire a thickness of a breast in a pressed state by a pressing member;
in a case where an ultrasound image of the breast in the pressed state is captured, acquire depth information indicating a depth to which imaging by at least one ultrasonography apparatus which captures the ultrasound image is possible;
derive imaging information indicating whether or not capture of an ultrasound image having predetermined accuracy or higher is possible by the at least one ultrasonography apparatus on the basis of the thickness of the breast and the depth information; and
output the imaging information;
wherein:
the control device is connected to a plurality of the ultrasonography apparatuses, each having a different limit depth,
the processor is configured to acquire the depth information of each of the plurality of the ultrasonography apparatuses, and
the processor is configured to derive the depth information for each of the plurality of ultrasonography apparatuses.

* * * * *